United States Patent
Tashiro et al.

(10) Patent No.: US 10,401,507 B2
(45) Date of Patent: Sep. 3, 2019

(54) COLLIMATOR, RADIATION DETECTOR, AND RADIATION EXAMINATION APPARATUS

(71) Applicants: Kabushiki Kaisha Toshiba, Minato-ku (JP); Toshiba Medical Systems Corporation, Otawara-shi (JP)

(72) Inventors: Hiroki Tashiro, Yokohama (JP); Hideshi Nakano, Yokosuka (JP); Tooru Tanaka, Fujisawa (JP); Aya Watase, Kawasaki (JP); Shuya Nambu, Nasushiobara (JP)

(73) Assignees: Kabushiki Kaisha Toshiba, Minato-ku (JP); Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/512,608

(22) PCT Filed: Feb. 28, 2017

(86) PCT No.: PCT/JP2017/007919
§ 371 (c)(1),
(2) Date: Mar. 20, 2017

(87) PCT Pub. No.: WO2017/163788
PCT Pub. Date: Sep. 28, 2017

(65) Prior Publication Data
US 2018/0120450 A1    May 3, 2018

(30) Foreign Application Priority Data

Mar. 24, 2016  (JP) ................................ 2016-060716
Feb. 28, 2017  (JP) ................................ 2017-036317

(51) Int. Cl.
*A61B 6/03*    (2006.01)
*G01T 1/20*    (2006.01)
(Continued)

(52) U.S. Cl.
CPC ............ *G01T 1/2002* (2013.01); *A61B 6/032* (2013.01); *A61B 6/035* (2013.01); *A61B 6/4291* (2013.01);
(Continued)

(58) Field of Classification Search
CPC ..... A61B 6/035; A61B 6/4291; A61B 6/4014; G21K 1/025; G21K 1/02; G02B 27/30; G01N 2223/316
See application file for complete search history.

(56) References Cited

U.S. PATENT DOCUMENTS 4,340,818 A * 7/1982 Barnes .................... A61B 6/06
378/155
5,099,134 A * 3/1992 Hase ...................... G21K 1/025
250/363.1
(Continued)

FOREIGN PATENT DOCUMENTS

| JP | 2000-338254 A | 12/2000 |
|---|---|---|
| JP | 2008-275362 A | 11/2008 |
| JP | 2012-86006 A | 5/2012 |

OTHER PUBLICATIONS

International Search Report dated May 23, 2017 in PCT/JP2017/007919 (with English Translation of Categories of Cited Documents).

*Primary Examiner* — David J Makiya
*Assistant Examiner* — Soorena Kefayati
(74) *Attorney, Agent, or Firm* — Oblon, McClelland, Maier & Neustadt, L.L.P.

(57) ABSTRACT

A collimator includes a plurality of modules each of which has a grid formation and in each of which a plurality of walls are arranged in a row in a first direction and a second (Continued)

direction intersecting the first direction. The plurality of modules are connected together by one or more connecting parts.

7 Claims, 14 Drawing Sheets

(51) Int. Cl.
    *A61B 6/00*         (2006.01)
    *G21K 1/02*        (2006.01)
    *A61B 6/06*         (2006.01)

(52) U.S. Cl.
    CPC .......... *A61B 6/5258* (2013.01); *A61B 6/5282* (2013.01); *G01T 1/2018* (2013.01); *G21K 1/025* (2013.01); *A61B 6/06* (2013.01); *A61B 6/4035* (2013.01); *A61B 6/4266* (2013.01); *A61B 6/547* (2013.01)

(56) References Cited

U.S. PATENT DOCUMENTS

| | | | | |
|---|---|---|---|---|
| 5,949,850 | A * | 9/1999 | Tang | G03F 7/0007 378/145 |
| 6,707,884 | B1 * | 3/2004 | Ogawa | G21K 1/025 378/154 |
| 7,149,284 | B2 * | 12/2006 | Ikhlef | G01T 1/1648 378/149 |
| 7,831,024 | B2 * | 11/2010 | Metzler | G02B 27/30 250/363.1 |
| 8,976,935 | B2 * | 3/2015 | Singh | G21K 1/02 250/363.1 |
| 2007/0025518 | A1 * | 2/2007 | Levene | A61B 6/032 378/149 |
| 2007/0025519 | A1 * | 2/2007 | Vogtmeier | G21K 1/02 378/149 |
| 2007/0064878 | A1 * | 3/2007 | Heismann | G21K 1/025 378/154 |
| 2007/0152159 | A1 * | 7/2007 | Short | G01T 1/1642 250/363.1 |
| 2008/0088059 | A1 * | 4/2008 | Tang | G21K 1/025 264/261 |
| 2011/0019801 | A1 * | 1/2011 | Eichenseer | G01T 1/2985 378/147 |
| 2011/0129069 | A1 * | 6/2011 | Freund | G21K 1/025 378/147 |
| 2011/0233412 | A1 | 9/2011 | Kawaguchi et al. | |
| 2011/0274252 | A1 * | 11/2011 | Kuwabara | A61B 6/4291 378/155 |
| 2012/0069954 | A1 * | 3/2012 | Iso | A61B 6/03 378/7 |
| 2012/0087462 | A1 * | 4/2012 | Ikhlef | A61B 6/00 378/4 |
| 2012/0132834 | A1 * | 5/2012 | Freund | G21K 1/025 250/505.1 |
| 2012/0219107 | A1 * | 8/2012 | Kurochi | G21K 1/025 378/19 |
| 2012/0307963 | A1 * | 12/2012 | Watanabe | A61B 6/4291 378/7 |
| 2013/0070892 | A1 * | 3/2013 | Mori | A61B 6/032 378/7 |
| 2013/0223588 | A1 * | 8/2013 | Kurochi | A61B 6/06 378/19 |
| 2013/0235972 | A1 * | 9/2013 | Kuroiwa | G21K 1/025 378/19 |
| 2013/0322603 | A1 * | 12/2013 | Kurochi | G21K 1/025 378/147 |
| 2014/0355734 | A1 * | 12/2014 | Ying | A61B 6/032 378/7 |
| 2015/0146842 | A1 * | 5/2015 | Kurochi | G21F 1/00 378/4 |
| 2016/0078972 | A1 * | 3/2016 | Reitz | G21K 1/025 378/147 |

\* cited by examiner

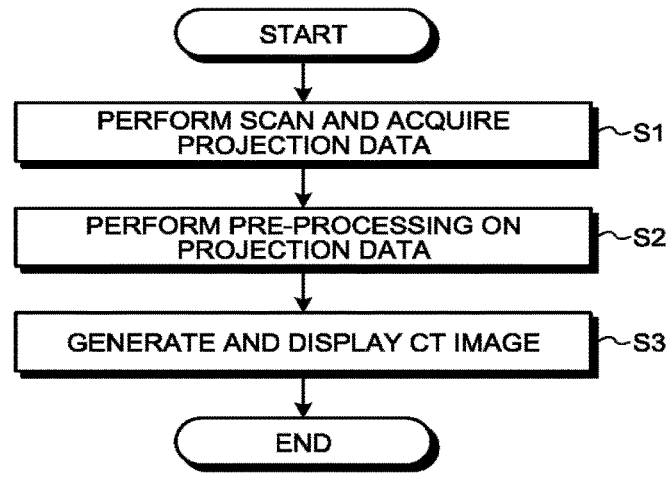
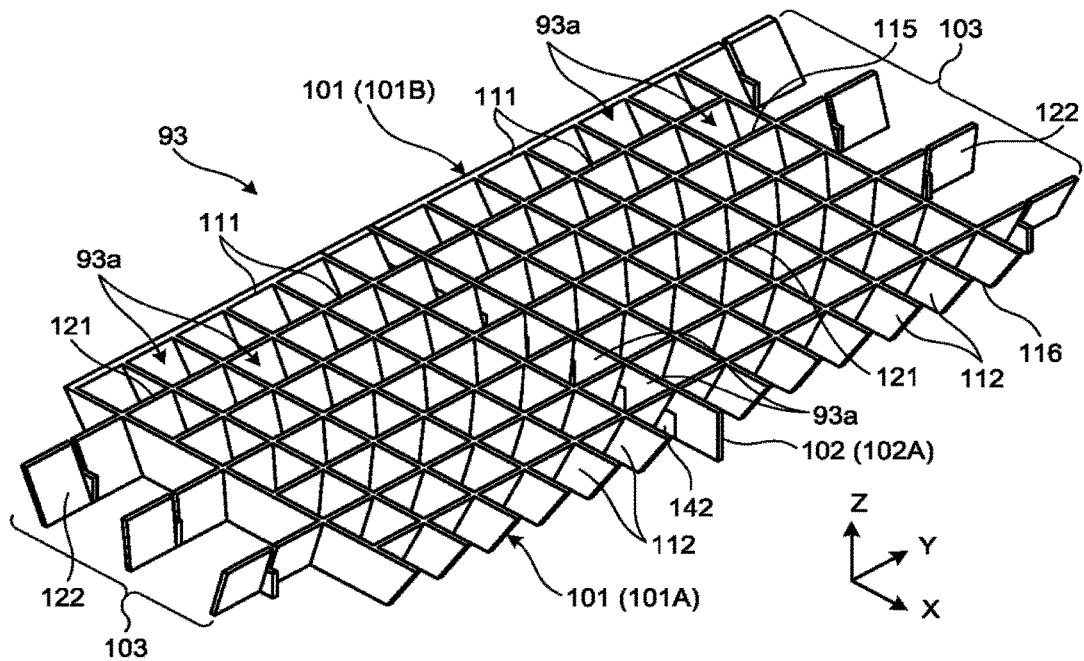

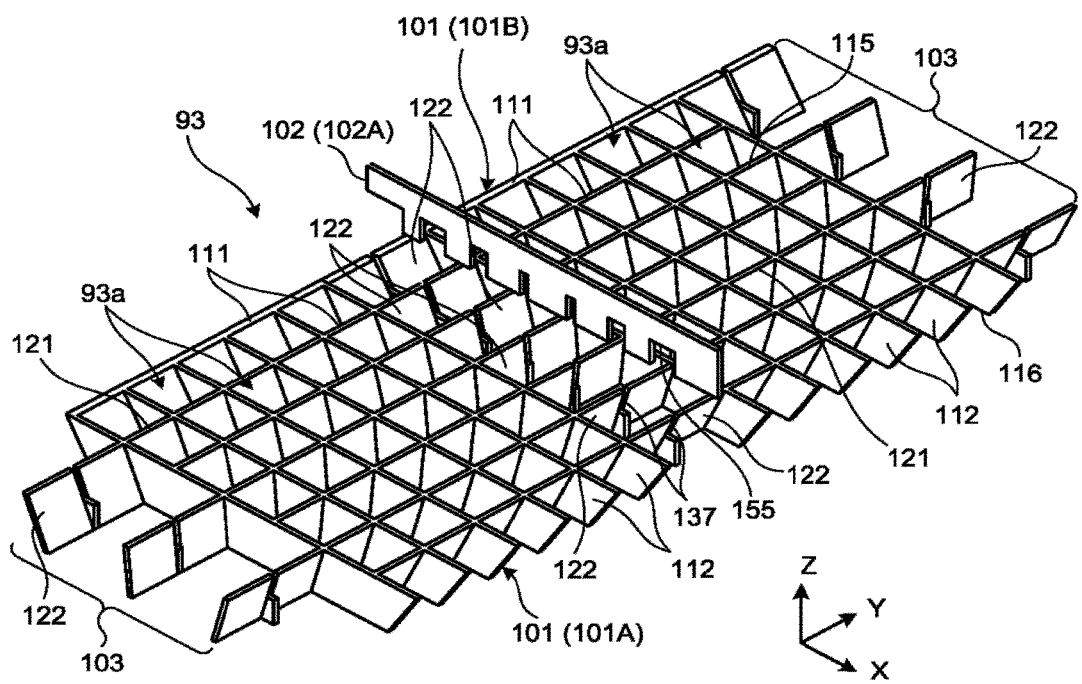
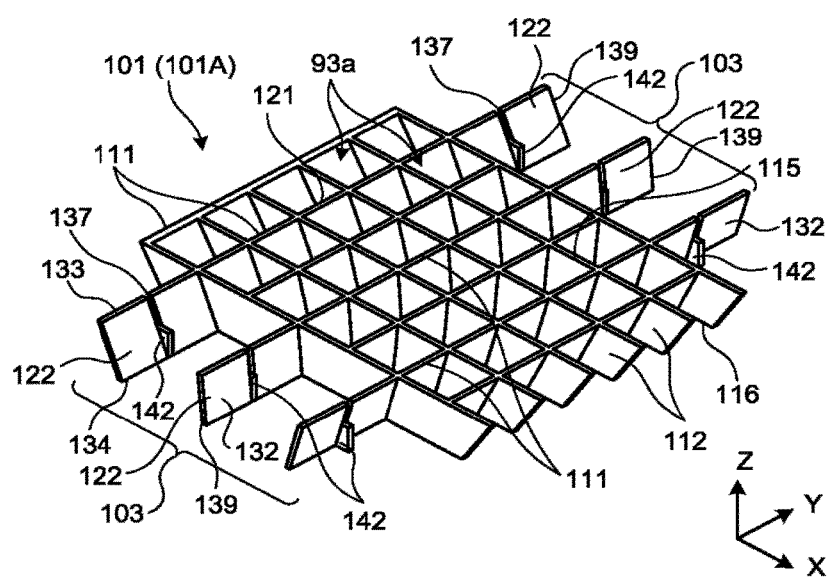

COLLIMATOR, RADIATION DETECTOR, AND RADIATION EXAMINATION APPARATUS

CROSS-REFERENCE TO RELATED APPLICATIONS

This application is national stage application of International Application No. PCT/JP2017/007919, filed on Feb. 28, 2017, which designates the United States, incorporated herein by reference, and which is based upon and claims the benefit of priority from Japanese Patent Application No. 2016-060716, filed on Mar. 24, 2016 and Japanese Patent Application No. 2017-036317, filed on Feb. 28, 2017, the entire contents of which are incorporated herein by reference.

FIELD

Embodiments described herein relate generally to a collimator, a radiation detector, and a radiation examination apparatus.

BACKGROUND

Radiation examination apparatuses such as X-ray Computed Tomography (CT) apparatuses include a collimator attached to a device configured to detect X-rays. For example, the collimator is structured with walls that are arranged in one direction or in a grid formation and is configured to block scattered X-rays.

BRIEF DESCRIPTION OF DRAWINGS

FIG. 3 is a flowchart illustrating an example of a process performed by the X-ray CT apparatus according to the first embodiment.

FIG. 4 is a perspective view of a part of a collimator according to the first embodiment.

FIG. 5 is an exploded perspective view of the part of the collimator according to the first embodiment.

FIG. 6 is a perspective view of one of collimating structures according to the first embodiment.

DETAILED DESCRIPTION

A collimator according to an embodiment includes a plurality of modules each of which has a grid formation and in each of which a plurality of walls are arranged in a row in a first direction and a second direction intersecting the first direction. The plurality of modules are connected together by one or more connecting parts.

A first embodiment will be explained below, with reference to FIGS. 1 to 13. In the present disclosure, some of the constituent elements in the embodiments and the explanations of the constituent elements may be expressed by using two or more mutually-different terms. The constituent elements and the explanations thereof that are expressed by using the two, or more mutually-different terms may be expressed by using other terms that are not mentioned in the present disclosure. Further, other constituent elements and explanations that are not expressed by using two or more mutually-different terms may also be expressed by using other terms that are not mentioned in the present disclosure.

Figure 1:
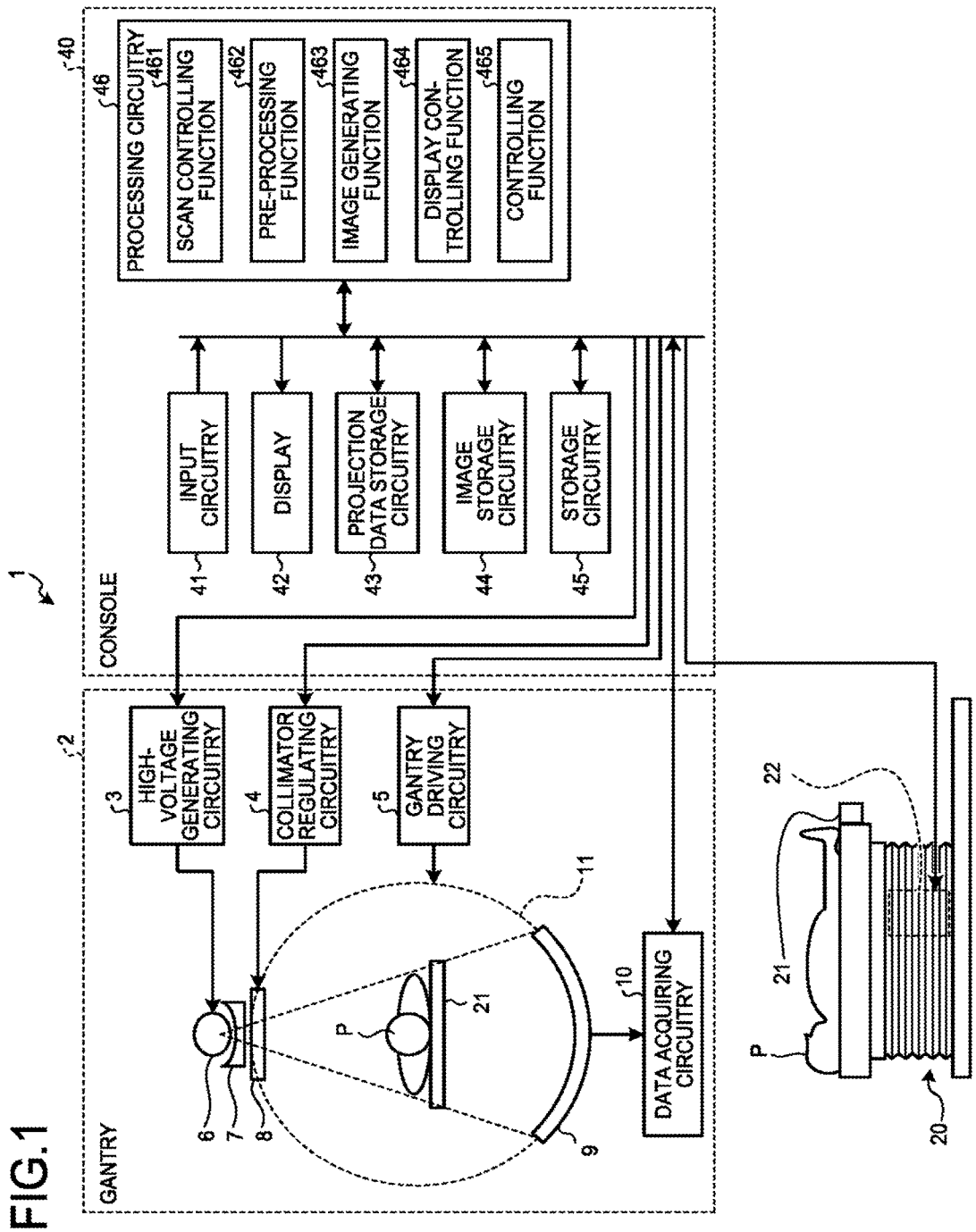
FIG. 1 is a diagram illustrating an exemplary configuration of an X-ray CT apparatus according to a first embodiment.

FIG. 1 is a diagram illustrating an exemplary configuration of an X-ray Computed Tomography (CT) apparatus 1 according to the first embodiment. The X-ray CT apparatus 1 is an example of a radiation examination apparatus. The radiation examination apparatus may be another type of apparatus. As illustrated in FIG. 1, the X-ray CT apparatus 1 includes a gantry 2, a couch 20, and a console 40. Possible configurations of the X-ray CT apparatus 1 are not limited to the configuration described below.

The gantry 2 includes high-voltage generating circuitry 3, collimator regulating circuitry 4, gantry driving circuitry 5, an X-ray tube 6, a wedge 7, a collimator 8, an X-ray detector 9, data acquiring circuitry 10, and a rotating frame 11. The X-ray tube 6 is an example of a radiation source. The X-ray detector 9 is an example of a radiation detector.

The high-voltage generating circuitry 3 is configured to supply an X-ray tube voltage to the X-ray tube 6. The collimator regulating circuitry 4 regulates the radiation range of the X-rays generated by the X-ray tube 6, by regulating the degree of opening and the position of the collimator 8. The gantry driving circuitry 5 is configured to rotate the rotating frame 11. The gantry driving circuitry 5 is thus configured to cause the X-ray tube 6 and the X-ray detector 9 to revolve on a circular orbit centered on a subject P. The high-voltage generating circuitry 3, the collimator regulating circuitry 4, and the gantry driving circuitry 5 may be realized by using one or more processors, for example.

The X-ray tube 6 is configured to radiate the X-rays toward the X-ray detector 9 and the subject P positioned between the X-ray tube 6 and the X-ray detector 9. The X-rays serve as an example of radiation. The radiation may be other types of radiation such as gamma rays. The X-ray tube 6 is configured to generate the X-rays by using the X-ray tube voltage supplied thereto by the high-voltage generating circuitry 3. The wedge 7 is an X-ray filter configured to adjust the dose of the X-rays radiated onto the subject P. The collimator 8 is a slit configured to adjust the radiation range of the X-rays radiated onto the subject P.

Figure 2:
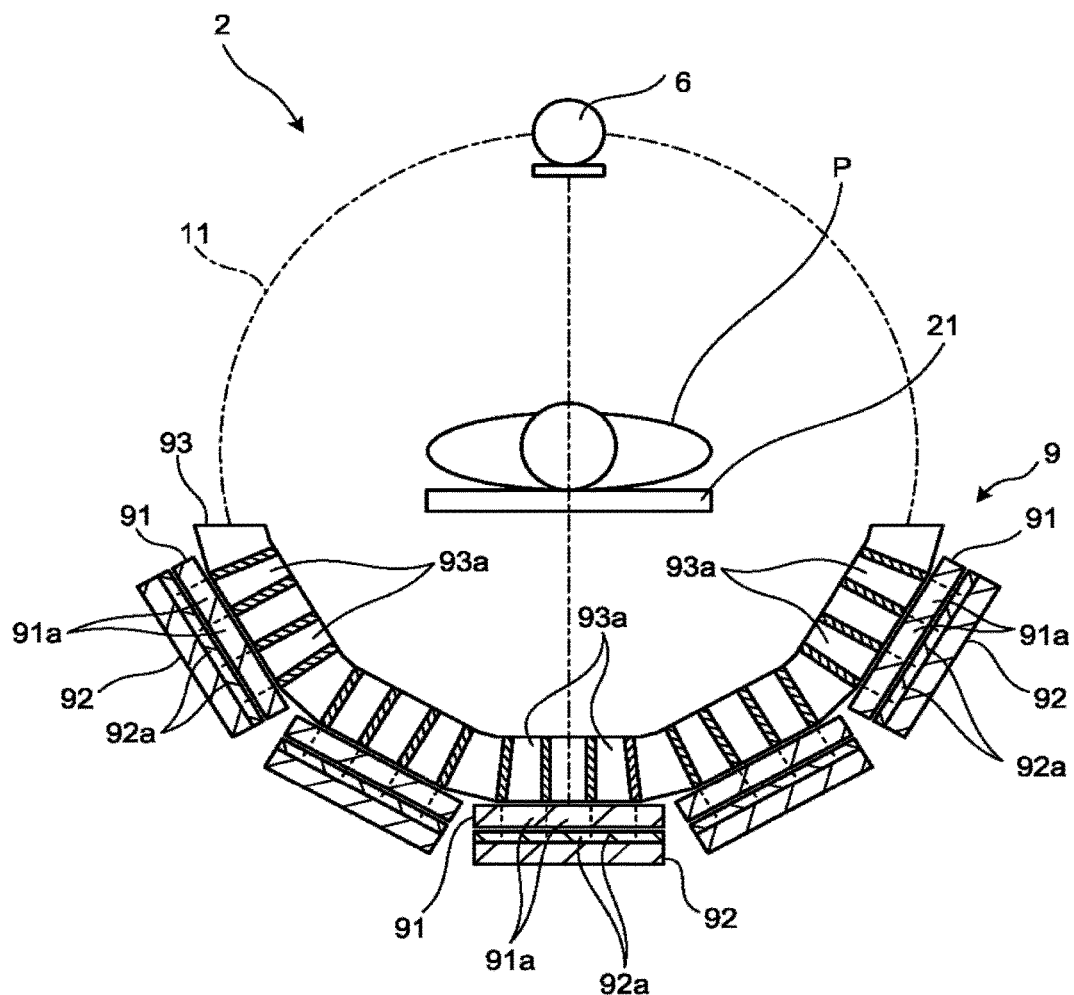
FIG. 2 is a schematic drawing of a gantry according to a first embodiment.

FIG. 2 is a schematic drawing of the gantry 2 according to the first embodiment. The X-ray detector 9 illustrated in FIG. 2 is configured to detect the X-rays radiated by the X-ray tube 6. The X-ray detector 9 includes a plurality of scintillator arrays 91, a plurality of photodiode arrays 92, and a collimator 93. The collimator 93 may be referred to as a rectifying device or a blocking (shielding) device (member).

The scintillator arrays 91 include a plurality of scintillators 91a that are arranged in two directions intersecting each other in a matrix formation. The plurality of scintillators 91a are, for example, arranged in the direction along a tangential line of the circumference of the rotating frame 11 and the direction along the body axis of the subject P. The scintillators 91a are configured to convert X-rays that have become incident thereto, into visible light. The scintillators 91a may be configured to convert not only X-rays but also other radiation into visible light.

For example, the scintillators 91a may be manufactured by using cadmium tungstate (CWO) or cesium iodide (CsI). Alternatively, the scintillators 91a may be manufactured by using other materials.

The photodiode arrays 92 include photodiodes 92a each of which is provided for a different one of the scintillators 91a. The photodiodes 92a serve as an example of a detecting part. Each of the plurality of photodiodes 92a faces a corresponding one of the scintillators 91a.

Each of the photodiodes 92a has an active area used for converting visible light emitted by the scintillators 91a into an electric signal. The electric signals are transmitted to the data acquiring circuitry 10. The active area may also be referred to as an anode. The photodiodes 92a are thus configured to detect the light.

The collimator 93 is structured with a plurality of plates to have a grid formation. For example, the collimator 93 is manufactured by using a material having a high atomic number and having a high X-ray blocking capability, such as tungsten or molybdenum. Alternatively, the collimator 93 may be manufactured by using other materials.

The collimator 93 is provided with a plurality of through openings 93a. The plurality of through openings 93a are, for example, holes oriented toward either the X-ray tube 6 or the subject P placed on the couch 20. The directions in which the plurality of through openings 93a are oriented are different from one another. The directions in which the plurality of through openings 93a are oriented are not limited to those in this example. Each of the plurality of scintillators 91a faces a corresponding one of the through openings 93a.

The X-rays radiated by the X-ray tube 6 pass through the subject P. The X-rays that have passed through the subject P go through the through openings 93a and become incident to the scintillators 91a. Also, a part of the X-rays may be scattered by the body of the subject P, for example. The collimator 93 blocks the scattered X-rays.

The data acquiring circuitry 10 illustrated in FIG. 1 is configured to generate projection data on the basis of the electric signals output by the photodiodes 92a. The projection data may represent a sinogram, for example. The sinogram is data obtained by arranging the signals detected by the photodiodes 92a in correspondence with different positions of the X-ray tube 6. In this situation, the positions of the X-ray tube 6 may be called views. The sinogram is data obtained by assigning effective energy levels of the X-rays detected by the photodiodes 92a to a two-dimensional rectangular (intersecting) coordinate system that uses a view direction and a channel direction as the axes thereof.

The data acquiring circuitry 10 is configured to store the generated sinogram into projection data storage circuitry 43 (explained later). The data acquiring circuitry 10 is included in a Data Acquisition System (DAS). Further, the data acquiring circuitry 10 is realized by using a processor, for example.

The rotating frame 11 is an annular-shaped frame. The rotating frame 11 is configured to support the X-ray tube 6 and the X-ray detector 9 so as to oppose each other. The rotating frame 11 is driven by the gantry driving circuitry 5 and is configured to rotate while being centered on the subject P.

The couch 20 includes a couchtop 21 and a couch driving circuitry 22. The couchtop 21 is a plate-like member on which the subject P is placed. By moving the couchtop 21 on which the subject P is placed, the couch driving circuitry 22 moves the subject P into an image taking opening of the gantry 2. Further, the couch driving circuitry 22 is realized by using a processor, for example.

The console 40 includes input circuitry 41, a display 42, projection data storage circuitry 43, an image storage circuitry 44, storage circuitry 45, and processing circuitry 46.

The input circuitry 41 is used by a user who inputs instructions and settings. The input circuitry 41 is included in a mouse or a keyboard, for example. The input circuitry 41 is configured to transfer the instructions and the settings input by the user to the processing circuitry 46. The input circuitry 41 is realized by using a processor, for example.

The display 42 is a monitor referenced by the user. For example, the display 42 is configured to receive, from the processing circuitry 46, an instruction to display a CT image and/or a Graphical User Interface (GUI) used by the user to input the instructions and the settings. On the basis of the instruction, the display 42 displays the CT image and/or the GUI.

The projection data storage circuitry 43 is configured to store therein the projection data generated by the data acquiring circuitry 10 and raw data generated by a pre-processing function 462 (explained later). The image storage circuitry 44 is configured to store therein a CT image generated by an image generating function 463 (explained later).

The storage circuitry 45 stores therein a computer program (hereinafter, "program") used by the high-voltage generating circuitry 3, the collimator regulating circuitry 4, the gantry driving circuitry 5, and the data acquiring circuitry 10 to realize the functions described above. The storage circuitry 45 stores therein a program used by the couch driving circuitry 22 to realize the functions described above. The storage circuitry 45 stores therein programs used by the processing circuitry 46 to realize each of the functions of a scan controlling function 461, the pre-processing function 462, the image generating function 463, a display controlling function 464, a controlling function 465, and other functions. Accordingly, the high-voltage generating circuitry 3, the collimator regulating circuitry 4, the gantry driving circuitry 5, the data acquiring circuitry 10, the couch driving circuitry 22, and the processing circuitry 46 realize the functions thereof, as a result of reading and executing the programs stored in the storage circuitry 45.

Further, the projection data storage circuitry 43, the image storage circuitry 44, and the storage circuitry 45 have a storage medium from which it is possible to read stored information by using a computer. The storage medium may be a hard disk, for example.

The processing circuitry 46 includes the scan controlling function 461, the pre-processing function 462, the image generating function 463, the display controlling function 464, and the controlling function 465. Details of these functions will be explained later. The processing circuitry 46 is realized by using a processor, for example.

FIG. 3 is a flowchart illustrating an example of a process performed by the X-ray CT apparatus 1 according to the first embodiment. The example of the process performed by the X-ray CT apparatus 1 according to the first embodiment will be explained, with reference to FIG. 3.

As illustrated in FIG. 3, the processing circuitry 46 performs a scan and acquires projection data (step S1). For example, the processing circuitry 46 reads and executes the program corresponding to the scan controlling function 461 from the storage circuitry 45.

The scan controlling function 461 is a function configured to control the X-ray CT apparatus 1 to perform scans. For example, by executing the scan controlling function 461, the processing circuitry 46 controls the X-ray CT apparatus 1 as described below.

By controlling the couch driving circuitry 22, the processing circuitry 46 moves the subject P into the image taking opening of the gantry 2. The processing circuitry 46 causes the gantry 2 to perform the scan on the subject P. More specifically, by controlling the high-voltage generating circuitry 3, the processing circuitry 46 causes the X-ray tube voltage to be supplied to the X-ray tube 6.

By controlling the collimator regulating circuitry 4, the processing circuitry 46 adjusts the degree of opening and the position of the collimator 8. Further, by controlling the gantry driving circuitry 5, the processing circuitry 46 causes the rotating frame 11 to rotate. Also, by controlling the data acquiring circuitry 10, the processing circuitry 46 causes the data acquiring circuitry 10 to acquire the projection data. The scan performed by the X-ray CT apparatus 1 may be, for example, a conventional scan, a helical scan, or a step-and-shoot scan.

Subsequently, the processing circuitry 46 performs preprocessing on the acquired projection data (step S2). For example, the processing circuitry 46 reads and executes the program corresponding to the pre-processing function 462 from the storage circuitry 45.

The pre-processing function 462 is a function configured to correct the projection data generated by the data acquiring circuitry 10. The correction may be, for example, a logarithmic conversion, an off-set correction, a sensitivity correction, a beam hardening correction, and/or a scattered ray correction.

The projection data corrected by the pre-processing function 462 is stored into the projection data storage circuitry 43. The projection data corrected by the pre-processing function 462 may be referred to as raw data.

After that, the processing circuitry 46 generates a CT image from the raw data and displays the generated CT image (step S3). For example, the processing circuitry 46 reads and executes the program corresponding to the image generating function 463 from the storage circuitry 45.

The image generating function 463 is a function configured to reconstruct the raw data stored in the projection data storage circuitry 43 and to generate the CT image. The reconstruction method may be, for example, a back projection process or a successive approximation method.

The processing circuitry 46 reads and executes the program corresponding to the display controlling function 464 from the storage circuitry 45. The display controlling function 464 is a function configured to cause the display 42 to display the CT image stored in the image storage circuitry 44.

Further, when executing the processes described above, the processing circuitry 46 reads and executes the program corresponding to the controlling function 465 from the storage circuitry 45, as appropriate. The controlling function 465 includes, among other functions, a function of causing constituent elements of the gantry 2, the couch 20, and the console 40 to operate with appropriate timing according to the purposes thereof.

Next, the collimator 93 included in the X-ray detector 9 will be explained in detail. In the first embodiment, the collimator 93 includes a plurality of modules each of which has a grid formation and in each of which a plurality of walls are arranged in a row in a first direction and a second direction intersecting the first direction, while the plurality of modules are connected together by connecting parts. In this situation, the connecting parts are realized with at least one plate-like member that is provided at an end of each of the plurality of modules and that projects in the first direction. Further, the plurality of modules are connected together by combining, in a grid formation, a connector with the connecting parts provided between any two of the modules positioned adjacent to each other, the connecting parts each being provided for a different one of the two modules.

FIG. 4 is a perspective view of a part of the collimator 93 according to the first embodiment. FIG. 5 is an exploded perspective view of the part of the collimator 93 according to the first embodiment. The collimator 93 includes a plurality of collimating structures 101 and a plurality of connecting tools 102. The collimating structures 101 serve as an example of modules. The connecting tools 102 serve as an example of the connector and the fifth wall.

The collimator 93 according to the first embodiment is formed by the plurality of collimating structures 101 and the connecting tools 102 each connecting collimating structures 101 positioned adjacent to each other. The collimator 93 may include other component parts.

FIGS. 4 and 5 illustrate two collimating structures 101A and 101B that are among the plurality of collimating structures 101 and one connecting tool 102. In the following sections, any description that is common to the plurality of collimating structures 101 will be provided as a description of the collimating structures 101. An individual description of the collimating structure 101A or the collimating structure 101B will be provided as a description of the collimating structure 101A or the collimating structure 101B.

The collimating structures 101 and the connecting tools 102 are manufactured by using, for example, a material having a high atomic number and having a high X-ray blocking capability such as tungsten or molybdenum. The collimating structures 101 and the connecting tools 102 are manufactured by using mutually the same material. However, the collimating structures 101 and the connecting tools 102 may be manufactured by using other materials and may be manufactured by using mutually-different materials.

In the first embodiment, one of the adjacently-positioned collimating structures 101 includes, as a plurality of walls, a plurality of first walls that are arranged in a row at intervals in a second direction and a plurality of third walls that are arranged in a row at intervals in a first direction and also includes, as a connecting part 103, at least one first extension part having a first opening and being provided at an end of at least one of the plurality of first walls. Further, the other of the adjacently-positioned collimating structures 101 includes, as a plurality of walls, a plurality of second walls that are arranged in a row at intervals in the second direction and a plurality of fourth walls that are arranged in a row at intervals in the first direction and also includes, as a connecting part 103, at least one second extension part having a second opening and being provided at an end of at least one of the plurality of second walls. Further, the connecting tool 102 is configured to be fitted in the first opening formed in the plurality of first walls and the second opening formed in the plurality of second walls.

FIG. 6 is a perspective view of the collimating structure 101A according to the first embodiment. As illustrated in FIG. 6, each of the collimating structures 101 has a plurality of first plates 111 and a plurality of second plates 112. The first plates 111 of the collimating structure 101A serve as an example of the first walls. The second plates 112 of the collimating structure 101A serve as an example of the second walls.

In the following explanations, the X-, Y-, and Z-axes in the drawings will be used for reference. The X-, Y-, and Z-axes are virtually defined with respect to any two collimating structures 101 that are positioned adjacent to each other, such as the collimating structures 101A and 101B. In other words, the X-, Y-, and Z-axes that are used for reference in the description of the collimating structures 101A and 101B may be different from the X-, Y-, and Z-axes that are used for reference in the description of other pairs of collimating structures 101. The X-axis, the Y-axis, and the Z-axis are orthogonal to (intersect) one another.

Each of the plurality of first plates 111 extends in a direction along the Y-axis. The direction along the Y-axis serves as an example of the first direction. The plurality of first plates 111 are arranged in a row at intervals in a direction along the X-axis. The direction along the X-axis serves as an example of the second direction.

Each of the plurality of second plates 112 extends in the direction along the X-axis. The plurality of second plates 112 are arranged in a row at intervals in the direction along the Y-axis. The plurality of second plates 112 are integrally formed with the plurality of first plates 111 and are configured to connect the plurality of first plates 111 together. In other words, the plurality of second plates 112 are formed together with the plurality of first plates 111. The plurality of second plates 112 are connected and fixed to the plurality of first plates 111.

The plurality of first plates 111 and the plurality of second plates 112 are combined together in a grid formation so as to form the plurality of through openings 93a. Each of the plurality of through openings 93a is oriented in a direction extending approximately along the Z-axis, but the plurality of through openings 93a are oriented in mutually-different directions.

Each of the collimating structures 101 has a top face 115 and a bottom face 116. The terms "top face 115" and "bottom face 116" are based on the top and bottom positional relationship in the drawings and do not limit the positions of the top face 115 and the bottom face 116.

The top face 115 is one end of each of the collimating structures 101 in terms of the direction along the Z-axis. The bottom face 116 is the other end of each of the collimating structures 101 in terms of the direction along the Z-axis. In other words, the top face 115 and the bottom face 116 are each an end in the thickness direction of each of the collimating structures 101.

The top face 115 and the bottom face 116 of the collimating structure 101A are formed as flat planes parallel to each other. In other words, in the direction along the Z-axis, the distance between the top face 115 and the bottom face 116 of the collimating structure 101A is constant. Consequently, in the direction along the Z-axis, the length of each of the plurality of first plates 111 is substantially equal to the length of each of the plurality of second plates 112 in the collimating structure 101A.

For example, the top face 115 is oriented toward either the X-ray tube 6 or the subject P placed on the couch 20. For example, the bottom face 116 is oriented toward the scintillator arrays 91. Each of the through openings 93a extends through the collimating structures 101 from the top face 115 to the bottom face 116.

At least one of the plurality of first plates 111 has a first part 121 and two second parts 122. The second parts 122 of the collimating structure 101A serve as an example of the first extension parts.

The rest of the plurality of first plates 111 each have a first part 121, but have no second part 122. Alternatively, at least one of the first plates 111 may have a first part 121 and a single second part 122.

The first plates 111 each having the first part 121 and the second parts 122 and the first plates 111 each having only the first part 121 are arranged so as to alternate. However, the positional arrangements of the first plates 111 are not limited to those in this example.

The first part 121 and the two second parts 122 extend continuously in the direction along the Y-axis. In a single collimating structure 101, the first part 121 is positioned between one of the plurality of arranged second plates 112 positioned at one end and another one of the plurality of arranged second plates 112 positioned at the other end.

The first parts 121 of the plurality of first plates 111 are combined with the plurality of second plates 112 in a grid formation. In other words, the plurality of second plates 112 are formed together with the first parts 121 of the first plates 111 so as to intersect the first parts 121. The first parts 121 of the plurality of first plates 111 and the plurality of second plates 112 form the plurality of through openings 93a.

Each of the two second parts 122 extends from a different one of the two ends, in terms of the direction along the Y-axis, of the first part 121. In other words, the second parts 122 are connected to either end of the first part 121 in terms of the direction along the Y-axis. That is to say, in a single collimating structure 101, the second parts 122 project from the second plates 112 positioned at either end among the plurality of arranged second plates 112.

Figure 7:
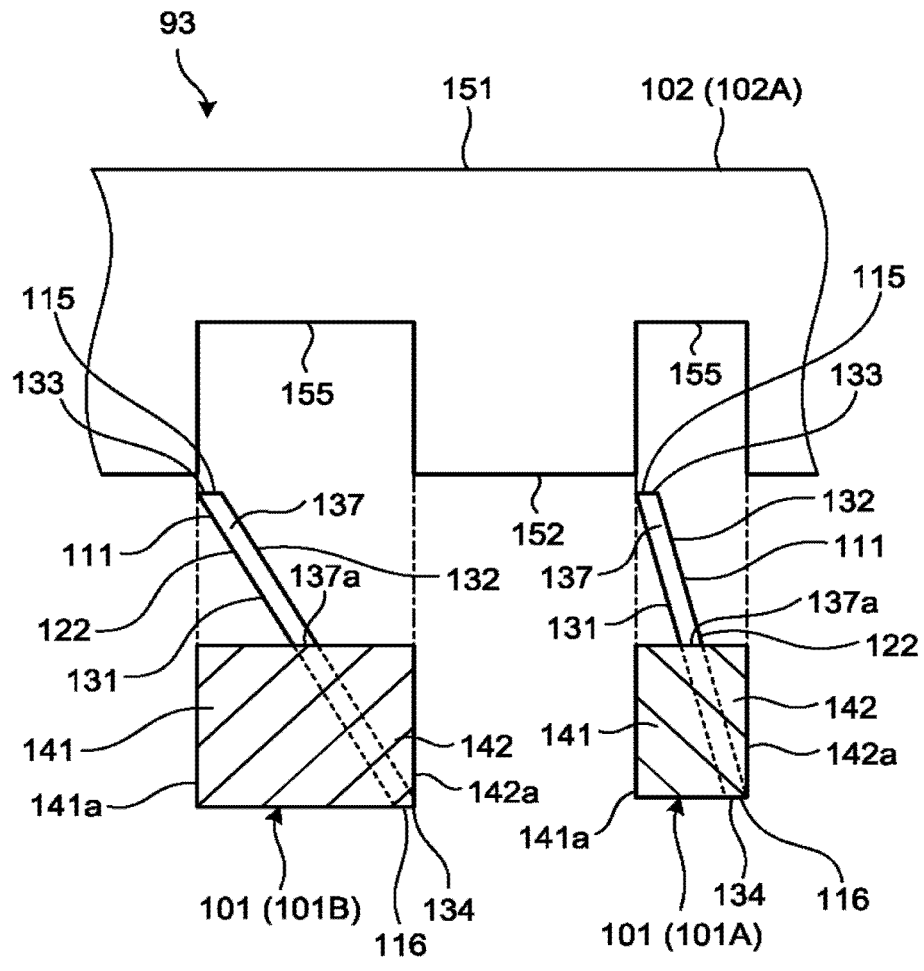
FIG. 7 is a cross-sectional view of a part of the collimator according to the first embodiment.

FIG. 7 is a cross-sectional view of a part of the collimator 93 according to the first embodiment. As illustrated in FIG. 7, the first plate 111 has a first lateral face 131, a second lateral face 132, an upper end 133, and a lower end 134.

The first lateral face 131 of the collimating structure 101A serves as an example of the first face. The upper end 133 of the collimating structure 101A serves as an example of the first end. The terms "upper end 133" and "lower end 134" are based on the upper and lower positional relationship in the drawings and do not limit the positions of the upper end 133 and the lower end 134.

The first part 121 of the first plate 111 has a first lateral face 131, a second lateral face 132, an upper end 133, and a lower end 134. Each of the two second parts 122 also has a first lateral face 131, a second lateral face 132, an upper end 133, and a lower end 134.

The first lateral face 131 is oriented in a direction intersecting the Y-axis. The first lateral face 131 is oriented approximately toward the adjacently-positioned first plate 111. For example, the first lateral face 131 of the collimating structure 101A is oriented in the direction that is orthogonal to (intersects) the Y-axis and that diagonally intersects the X-axis (i.e., diagonally downward in FIG. 7). In other words, when being viewed in a direction along the Z-axis, the first lateral face 131 is oriented toward the bottom face 116.

The second lateral face 132 is positioned on the opposite side of the first lateral face 131. Accordingly, the second lateral face 132 is oriented in a direction intersecting the Y-axis. The second lateral face 132 is oriented approximately toward the adjacently-positioned first plate 111. For example, the second lateral face 132 of the collimating structure 101A is oriented in the direction that is orthogonal to (intersects) the Y-axis and that diagonally intersects the X-axis (i.e., diagonally upward in FIG. 7).

Each of the first plates 111 having the first lateral face 131 and the second lateral face 132 described above extends in a direction diagonally intersecting the Z-axis, in a planar view in a direction along the Y-axis. The plurality of first plates 111 extend in mutually-different directions in a planar view in a direction along the Y-axis. In other words, the angle formed by the extending direction of one of the first plates 111 and the Z-axis is different from the angle formed by the extending direction of any other first plates 111 and the Z-axis.

Further, in a planar view in a direction along the X-axis, each of the second plates 112 extends in a direction along the Z-axis. The plurality of second plates 112 extend parallel to one another. Alternatively, in a planar view in a direction along the X-axis, the plurality of second plates 112 may extend in mutually-different directions.

The upper end 133 is an end of each of the first plates 111 in terms of the extending direction of the through openings 93a. In other words, the upper end 133 is an end of each of the first plates 111 in terms of the direction that is orthogonal to (intersects) the Y-axis and that extends along the first lateral face 131. The upper end 133 is also an end of each of the first plates 111 in terms of the direction along the Z-axis. The lower end 134 is positioned on the opposite side of the upper end 133. For example, the upper end 133 is oriented toward either the X-ray tube 6 or the subject P placed on the couch 20. For example, the lower end 134 is oriented toward the scintillator arrays 91.

The upper ends 133 of the plurality of the first plates 111 form the top face 115 of the collimating structures 101, together with the ends of the second plates 112 positioned on one side in terms of a direction along the Z-axis. The lower ends 134 of the plurality of first plates 111 form the bottom face 116 of the collimating structures 101, together with the ends of the second plates 112 positioned on the other side in terms of the direction along the Z-axis.

Each of the second parts 122 is provided with a slit 137. The slits 137 provided in the collimating structure 101A serve as an example of the first openings. Each of the slits 137 opens in a direction along the X-axis. In other words, each of the slits 137 extends through a corresponding one of the second parts 122 in the direction along the X-axis, from the first lateral face 131 to the second lateral face 132.

Each of the slits 137 further opens at the upper end 133. In other words, each of the slits 137 is a cut-out part extending from the upper end 133. Each of the slits 137 extends in a direction along the Z-axis from the upper end 133 toward the lower end 134.

Each of the second parts 122 of the first plates 111 has a first projecting wall 141 and a second projecting wall 142. The first projecting walls 141 of the collimating structure 101A serve as an example of the projection and the sixth wall. The first projecting walls 141 and the second projecting walls 142 are disposed in the same positions as the slits 137 are, in terms of a direction along the Y-axis.

Each of the first projecting walls 141 projects from a corresponding one of the first lateral faces 131 in a direction along the X-axis. In other words, each of the first projecting walls 141 projects from a corresponding one of the first lateral faces 131 toward the adjacently-positioned first plate 111. Each of the first projecting walls 141 extends in a direction along the Z-axis, similarly to each of the slits 137.

Each of the second projecting walls 142 projects from a corresponding one of the second lateral faces 132 in a direction along the X-axis. In other words, each of the second projecting walls 142 projects from a corresponding one of the first lateral faces 131 toward the adjacently-positioned first plate 111. Each of the second projecting walls 142 extends in a direction along the Z-axis, similarly to each of the slits 137.

Each of the slits 137 extends from the upper end 133 to a corresponding one of the first projecting walls 141 and a corresponding one of the second projecting walls 142. Each of the first projecting walls 141 and the second projecting walls 142 extends from a corresponding one of the slits 137 to the lower end 134.

In the direction along the X-axis, an end 141a of each of the first projecting walls 141 is substantially in the same position with the upper end 133. In terms of the direction along the X-axis, the end 141a of each of the first projecting walls 141 may be positioned farther from the first plate 111 than the upper end 133 is or may be substantially in the same position with an end 137a of a corresponding one of the slits 137.

In terms of the direction along the X-axis, an end 142a of each of the second projecting walls 142 is substantially in the same position with the lower end 134. In terms of the direction along the X-axis, the end 142a of each of the second projecting walls 142 may be positioned farther from the first plate 111 than the lower end 134 is or may be positioned closer to the end 137a of a corresponding one of the slits 137 than the lower end 134 is.

As illustrated in FIG. 6, each of the first plates 111 has two end faces 139. The two end faces 139 are the end faces of each of the first plates 111 in terms of a direction along the Y-axis. The end faces 139 are provided in the second parts 122.

Figure 8:
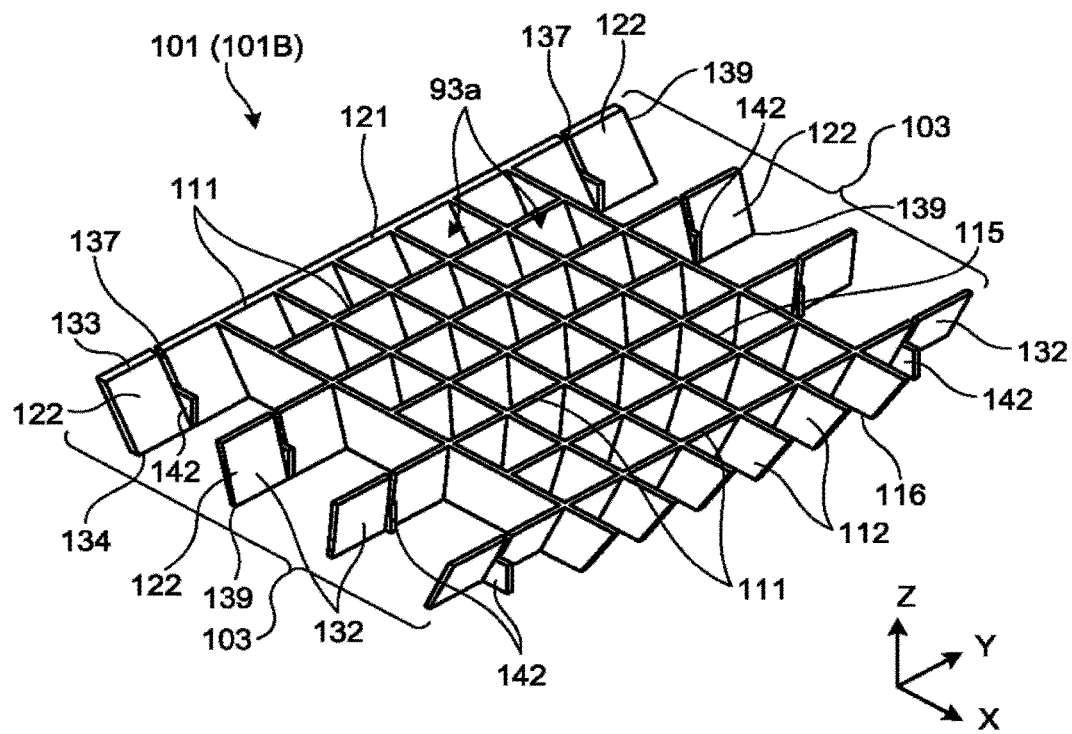
FIG. 8 is a perspective view of another one of the collimating structures according to the first embodiment.

FIG. 8 is a perspective view of the collimating structure 101B according to the first embodiment. The collimating structure 101B also has a plurality of first plates 111 and a plurality of second plates 112 described above. The first plates 111 of the collimating structure 101B serve as an example of the first walls. The second plates 112 of the collimating structure 101B serve as an example of the second walls.

As illustrated in FIG. 5, each of the second parts 122 of the collimating structure 101B is positioned between the second parts 122 of the collimating structure 101A that is positioned adjacent thereto in a direction along the X-axis. The second parts 122 of the collimating structure 101B each serve as an example of the second extension part.

In a direction along the X-axis, the second parts 122 of the collimating structure 101A and the second parts 122 of the collimating structure 101B are arranged so as to alternate. However, the positional arrangements of the second parts 122 of the collimating structures 101A and 101B are not limited to those in this example. For instance, it is also acceptable to arrange two or more second parts 122 of the collimating structure 101B to be positioned between adjacently-positioned second parts 122 of the collimating structure 101A.

As illustrated in FIG. 7, the second lateral face 132 in the collimating structure 101B is oriented approximately toward the first lateral face 131 in the adjacently-positioned collimating structure 101A. The first lateral face 131 in the collimating structure 101B is approximately oriented toward the second lateral face 132 in the adjacently-positioned collimating structure 101A. The first lateral face 131 of each of the second parts 122 in the collimating structure 101B serves as an example of the first face.

The slits 137 provided in the second parts 122 of the collimating structure 101A and the slits 137 provided in the second parts 122 of the collimating structure 101B are arranged in a row in a direction along the X-axis. The slits 137 provided in the collimating structure 101B serve as an example of the first openings. Further, the first projecting walls 141 and the second projecting walls 142 in the collimating structure 101A and the first projecting walls 141 and the second projecting walls 142 in the collimating structure 101B are arranged in a row in a direction along the X-axis.

The top face 115 and the bottom face 116 of the collimating structure 101B are formed as flat planes parallel to each other. In other words, in the direction along the Z-axis, the distance between the top face 115 and the bottom face 116 of the collimating structure 101B is constant. In the direction along the Z-axis, the length of each of the plurality of first plates 111 is substantially equal to the length of each of the plurality of second plates 112 in the collimating structure 101B.

Further, in the direction along the Z-axis, the length of each of the plurality of first plates 111 and each of the plurality of second plates 112 in the collimating structure 101A is substantially equal to the length of each of the plurality of first plates 111 and each of the plurality of second plates 112 in the collimating structure 101B. In other words, the thickness of the collimating structure 101A is substantially equal to the thickness of the collimating structure 101B. However, the thickness of the collimating structure 101A may be different from the thickness of the collimating structure 101B.

In a direction along the Z-axis, the length of each of the slits 137 formed in the collimating structure 101A is substantially equal to the length of each of the slits 137 formed in the collimating structure 1012. In other words, in the direction along the Z-axis, the length from the upper end 133 to the end 137a of each of the slits 137 in the collimating structure 101A is substantially equal to the length from the upper end 133 to the end 137a of each of the slits 137 in the collimating structure 101B. The upper end 133 of the collimating structure 101B serves as an example of the second end. Alternatively, in a direction along the Z-axis, the length of each of the slits 137 in the collimating structure 101A may be different from the length of each of the slits 137 in the collimating structure 101B.

The end faces 139 of the first plates 111 positioned on one side in the collimating structure 101B illustrated in FIG. 8 are in contact with the collimating structure 101A. For example, the end faces 139 of the first plates 111 positioned on the one side in the collimating structure 101B are in contact with the second plate 112 positioned at the end among the plurality of arranged second plates 112 in the collimating structure 101A.

Figure 9:
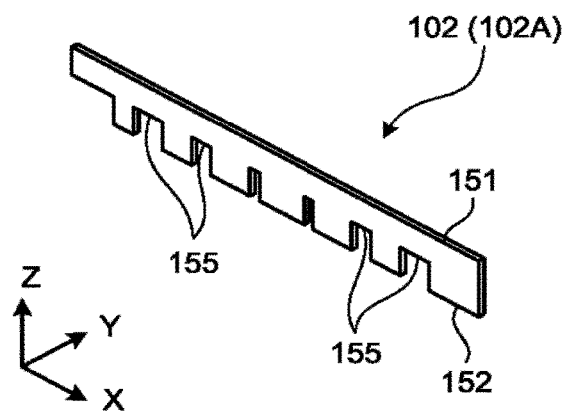
FIG. 9 is a perspective view of one of connecting tools according to the first embodiment.

FIG. 9 is a perspective view of the connecting tool 102 according to the first embodiment. As illustrated in FIG. 9, the connecting tool 102 is formed to have a plate-like shape. The thickness of the connecting tool 102 is substantially equal to the thickness of each of the first plates 111 and is also substantially equal to the thickness of each of the second plates 112. Alternatively, the connecting tool 102 may be formed to have a different shape, such as a bar-like shape.

A plurality of connecting tools 102 include a plurality of types of connecting tools 102 each having a shape corresponding to the collimating structure 101 connected thereby. FIG. 9 illustrates a connecting tool 102A connecting the collimating structure 101A and the collimating structure 101B together.

In the following sections, any description that is common to the plurality of connecting tools 102 will be provided as a description of the connecting tools 102. An individual description of the connecting tool 102A will be provided as a description of the connecting tool 102A.

The connecting tool 102A extends in a direction along the X-axis. In other words, the connecting tool 102A extends parallel to the plurality of second plates 112 in the collimating structure 101A and also extends parallel to the plurality of second plates 112 in the collimating structure 101B.

The connecting tool 102A has an upper end 151 and a lower end 152. The terms "upper end 151" and "lower end 152" are based on the upper and lower positional relationship in the drawings and do not limit the positions of the upper end 151 and the lower end 152.

The upper end 151 is one end of the connecting tool 102A in terms of the direction along the Z-axis. The lower end 152 is positioned on the opposite side of the upper end 151. For example, the upper end 151 is oriented toward either the X-ray tube 6 or the subject P placed on the couch 20. For example, the lower end 152 is oriented toward the scintillator arrays 91.

The distance between the upper end 151 and the lower end 152 is substantially equal to the length of each of the first plates 111 in the collimating structure 101A in a direction along the Z-axis and is substantially equal to the length of each of the second plates 112 in a direction along the Z-axis. Further, the distance between the upper end 151 and the lower end 152 is substantially equal to the length of each of the first plates 111 in the collimating structure 101B in a direction along the Z-axis and is substantially equal to the length of each of the second plates 112 in a direction along the Z-axis.

The connecting tool 102A is provided with a plurality of recesses 155. The recesses 155 serve as an example of cut-out parts and may also be referred to as openings, holes, or slits, for example. Each of the plurality of recesses 155 is a cut-out part that is substantially rectangular. However, each of the recesses 155 may be formed to have other shapes. Each of the recesses 155 opens at the lower end 152. In other words, each of the recesses 155 extends from the lower end 152 in a direction along the Z-axis.

As illustrated in FIG. 5, the connecting tool 102A is fitted into the slits 137 formed in the plurality of first plates 111 in the collimating structure 101A and the slits 137 formed in the plurality of first plates 111 in the collimating structure 101B. The connecting tool 102A is fitted into the plurality of slits 137 in a direction along the Z-axis.

When the connecting tool 102A has been fitted in the slits 137, the connecting tool 102A restricts the first plates 111 in the collimating structures 101A and 101B from moving in the direction along the Y-axis and the direction along the Z-axis.

As illustrated in FIG. 7, each of the recesses 155 has substantially the same shape as a corresponding one of the first projecting walls 141 and the second projecting walls 142. In other words, in a direction along the X-axis, the length of each of the recesses 155 is substantially equal to the distance between the end 141a of a corresponding one of the first projecting walls 141 and the end 142a of a corresponding one of the second projecting walls 142. Further, in a direction along the Z-axis, the length of each of the recesses 155 is substantially equal to the length of a corresponding one of the first projecting walls 141 and the second projecting walls 142.

Into the recesses 155 configured as described above, the corresponding first projecting walls 141 and the corresponding second projecting walls 142 are fitted. In other words, into each of the recesses 155, either a part of a corresponding one of the first plates 111 in the collimating structure 101A or a part of a corresponding one of the first plates 111 in the collimating structure 101B is fitted. When the first projecting walls 141 and the second projecting walls 142 have been fitted in the recesses 155, the connecting tool 102A restricts the first plates 111 in the collimating structures 101A and 101B from moving in the direction along the X-axis.

In the manner described above, the connecting tool 102A is fitted in the slits 137 formed in the collimating structures 101A and 101B, and the collimating structures 101A and 101B are fitted in the recesses 155 formed in the connecting tool 102A. As a result, the connecting tool 102A is attached to the collimating structures 101A and 101B so as to connect together the collimating structure 101A and the collimating structure 101B.

For example, the connecting tool 102A determines the positions of the collimating structure 101A and the collimating structure 101B. In that state, the collimating structures 101A and 101B and the connecting tool 102A are fixed to each other, by using an adhesive agent, for example. However, the collimating structures 101A and 101B and the connecting tool 102A may be fixed to each other by using other means. Alternatively, the collimating structures 101A and 101B and the connecting tool 102A do not necessarily have to be fixed to each other.

As illustrated in FIG. 4, when the connecting tool 102A has been attached to the collimating structures 101A and 101B, the connecting tool 102A, the first projecting walls 141, and the second projecting walls 142 form a single plate. Together with the first plates 111 and the second plates 112 in the collimating structures 101A and 101B, the connecting tool 102A, the first projecting walls 141, and the second projecting walls 142 form the plurality of through openings 93a.

Figure 10:
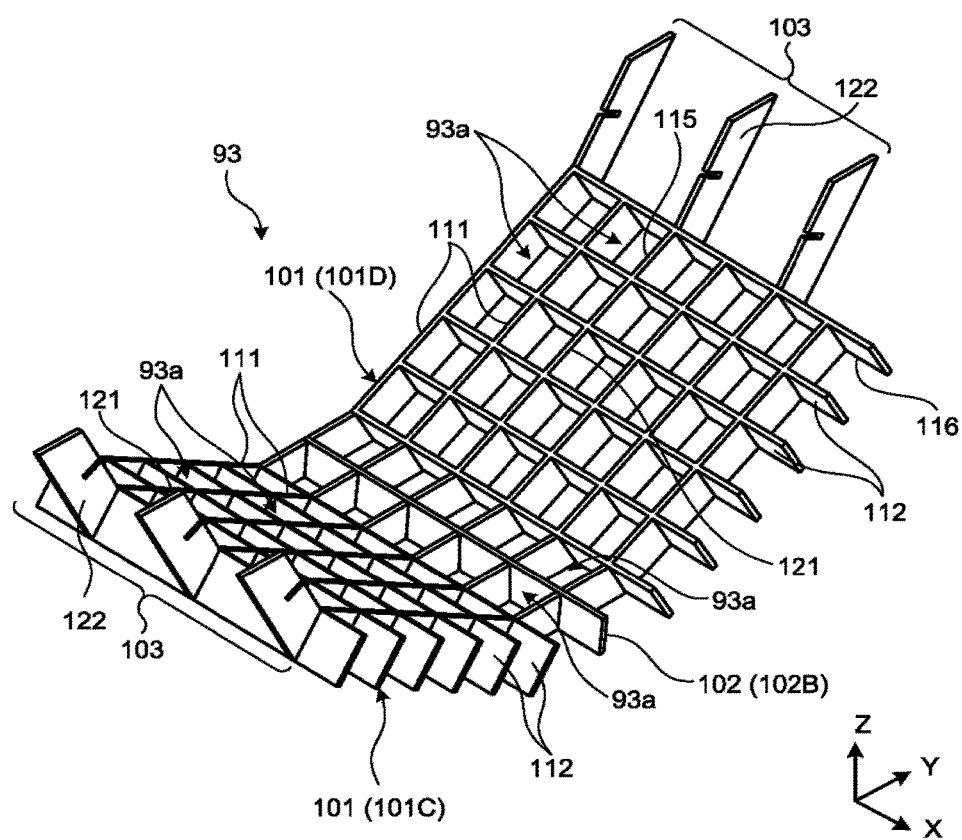
FIG. 10 is a perspective view of another part of the collimator according to the first embodiment.
Figure 11:
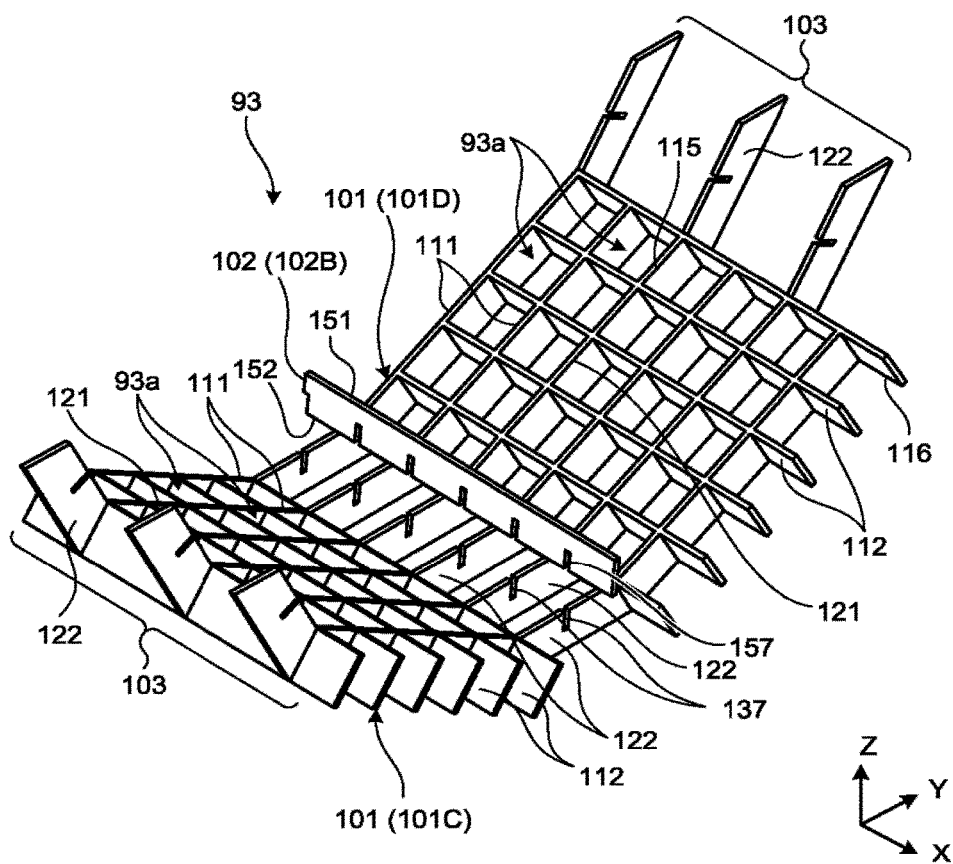
FIG. 11 is an exploded perspective view of said another part of the collimator according to the first embodiment.

FIG. 10 is a perspective view of another part of the collimator 93 according to the first embodiment. FIG. 11 is an exploded perspective view of said another part of the collimator 93 according to the first embodiment. As illustrated in FIG. 11, the collimator 93 includes other collimating structures 101C and 101D and another connecting tool 102B.

Figure 12:
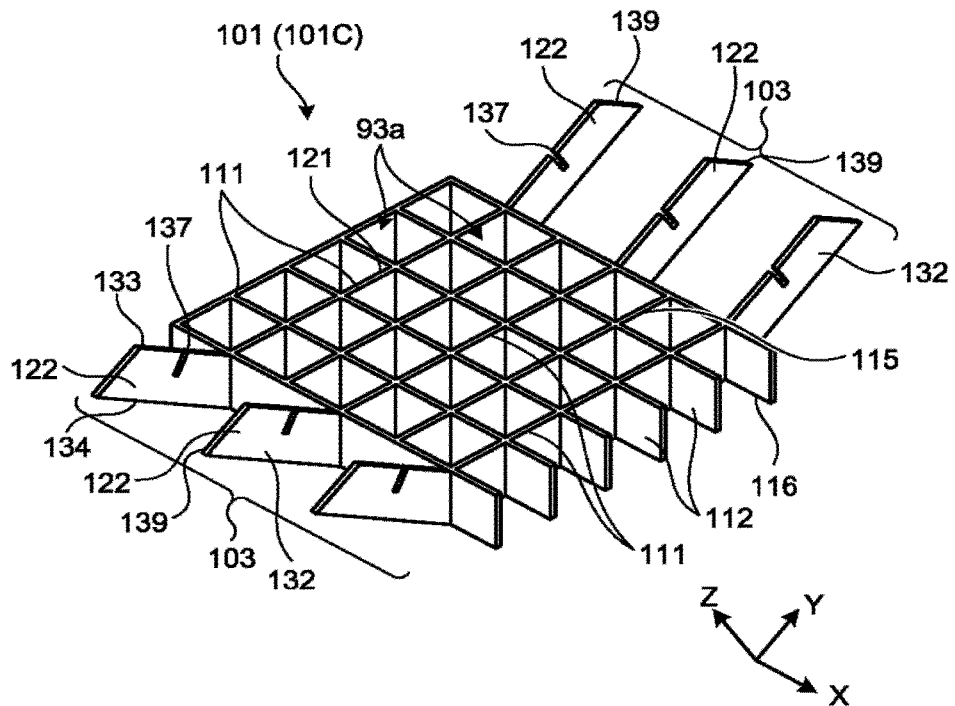
FIG. 12 is a perspective view of yet another one of the collimating structures according to the first embodiment.

FIG. 12 is a perspective view of the collimating structure 101C according to the first embodiment. As illustrated in FIG. 12, each of the first parts 121 in the collimating structure 101C extends in a direction diagonally intersecting the Y-axis. The first parts 121 in the collimating structure 101C serve as an example of the third extension part. The plurality of second plates 112 in the collimating structure 101C are arranged in a row at intervals in the extending direction of the first parts 121 and are attached and fixed to the first parts 121.

The second parts 122 positioned on one side of the collimating structure 101C extend in a direction along the Y-axis. In other words, the extending direction of the second parts 122 and the extending direction of the first parts 121 diagonally intersect each other. For example, the angle formed by the extending direction of the second parts 122 and the extending direction of the first parts 121 is larger than 0 degrees and smaller than 90 degrees. However, the angle formed by the extending direction of the second parts 122 and the extending direction of the first parts 121 may be 90 degrees.

In FIG. 12, the extending directions of the second parts 122 positioned on either side diagonally intersect the extending direction of the first parts 121. However, another arrangement is also acceptable in which the extending direction of the second parts 122 positioned on one side diagonally intersects the extending direction of the first parts 121, while the extending direction of the second parts 122 positioned on the other side is the same as the extending direction of the first parts 121.

In a planar view in a direction along the Y-axis, each of the second parts 122 of the first plates 111 in the collimating structure 101C extends in a direction along the Z-axis. The plurality of first plates 111 in the collimating structure 101C extend parallel to one another. However, in a planar view in a direction along the Y-axis, the plurality of first plates 111 may extend in mutually-different directions.

Figure 13:
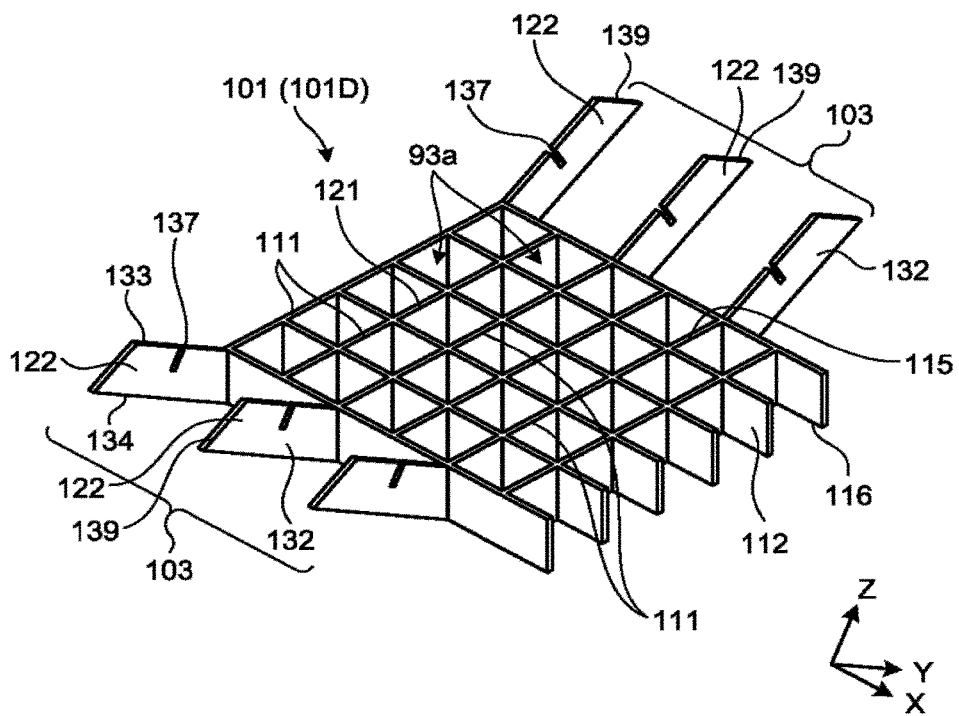
FIG. 13 is a perspective view of yet another one of the collimating structures according to the first embodiment.

FIG. 13 is a perspective view of the collimating structure 101D according to the first embodiment. As illustrated in FIG. 13, each of the first parts 121 in the collimating structure 101D extends in a direction diagonally intersecting the Y-axis. The plurality of second plates 112 in the collimating structure 101D are arranged in a row at intervals in the extending direction of the first parts 121 and are attached and fixed to the first parts 121.

Each of the second parts 122 positioned on one side of the collimating structure 101D extends in a direction along the Y-axis. In other words, the extending direction of the second parts 122 and the extending direction of the first parts 121 diagonally intersect each other. However, the angle formed by the extending direction of the second parts 122 and the extending direction of the first parts 121 in the collimating structure 101D may be different from the angle formed by the extending direction of the second parts 122 and the extending direction of the first parts 121 in the collimating structure 101C.

In FIG. 13, the extending directions of the second parts 122 positioned on either side diagonally intersect the extending direction of the first parts 121. However, another arrangement is also acceptable in which the extending direction of the second parts 122 positioned on one side diagonally intersects the extending direction of the first parts 121, while the extending direction of the second parts 122 positioned on the other side is the same as the extending direction of the first parts 121.

In a planar view in a direction along the Y-axis, each of the second parts 122 of the first plates 111 in the collimating structure 101D extends in a direction along the Z-axis. The plurality of first plates 111 in the collimating structure 101D extend parallel to one another. However, in a planar view in a direction along the Y-axis, the plurality of first plates 111 may extend in mutually-different directions.

As illustrated in FIG. 11, the connecting tool 102B extends in the direction along the X-axis. Similarly to the connecting tool 102A, the connecting tool 102B has an upper end 151 and a lower end 152. The connecting tool 102B has a plurality of slits 157. The slits 157 serve as an example of cut-out parts.

Each of the slits 157 opens at the lower end 152. In other words, each of the slits 157 extends from the lower end 152 in a direction along the Z-axis. The plurality of slits 157 are disposed substantially in the same positions as the slits 137 are in the collimating structures 101C and 101D, in terms of the direction along the X-axis.

The connecting tool 102B is fitted into the slits 137 formed in the plurality of first plates 111 in the collimating structure 101C and the slits 137 formed in the plurality of first plates 111 in the collimating structure 101D. The connecting tool 102B is fitted into the plurality of slits 137 in a direction along the Z-axis.

When the connecting tool 102B has been fitted in the slits 137, the connecting tool 102B restricts the first plates 111 in the collimating structures 101C and 101D from moving in the direction along the Y-axis and the direction along the Z-axis.

Further, into each of the slits 157 formed in the connecting tool 102B, one of the second parts 122 of the first plates 111 positioned on one side of the collimating structure 101C or one of the second parts 122 of the first plates 111 positioned on one side of the collimating structure 101D is fitted. When the second parts 122 have been fitted in the slits 157, the connecting tool 102B restricts the first plates 111 in the collimating structures 101C and 101D from moving in the direction along the X-axis.

In the manner described above, the connecting tool 102B is fitted in the slits 137 formed in the collimating structures 101C and 101D, and the second parts 122 of the collimating structures 101C and 101D are fitted in the slits 157 formed in the connecting tool 102B. As a result, the connecting tool 102B is attached to the collimating structures 101C and 101D so as to connect together the collimating structure 101C and the collimating structure 101D.

As illustrated in FIG. 10, when the connecting tool 102B has been attached to the collimating structures 101C and 101D, the connecting tool 102B forms the plurality of through openings 93a, together with the first plates 111 and the second plates 112 in the first and the second collimating structures 101C and 101D.

In the manner explained above, the plurality of collimating structures 101 are connected together by the connecting tools 102, so as to form the collimator 93. By combining the collimating structures 101A, 101B, 101C, and 101D together, the arch-shaped collimator 93 is formed.

To the collimator 93, the plurality of scintillator arrays 91 and the plurality of photodiode arrays 92 illustrated in FIG. 2 are attached by using an adhesive agent, for example. However, the plurality of scintillator arrays 91 and the plurality of photodiode arrays 92 may be attached to the collimator 93 by using other means.

For example, to one of the collimating structures 101 (e.g., 101A), one of the scintillator arrays 91 and one of the photodiode arrays 92 are attached. In other words, to the plurality of first plates 111 and the plurality of second plates 112 in the collimating structure 101A, one of the plurality of scintillators 91a is attached.

Further, to another one of the collimating structures 101 (e.g., 101B), another one of the scintillator arrays 91 and another one of the photodiode arrays 92 are attached. In other words, to the plurality of first plates 111 and the plurality of second plates 112 in the collimating structure 101B, another one of the plurality of scintillators 91a is attached.

The collimating structure 101A and the collimating structure 101B configured in this manner are connected together by the connecting tool 102A. As a result, the plurality of scintillator arrays 91 and the plurality of photodiode arrays 92 are connected together.

The collimating structures 101 and the connecting tools 102 according to the first embodiment may be formed by a laminate molding process by using a three-dimensional (3D) printer, for example. Accordingly, it is possible to easily manufacture the collimating structures 101 and the connecting tools 102. However, the collimating structures 101 and the connecting tools 102 do not necessarily have to be manufactured in this manner and may be manufactured by using other methods.

In the X-ray CT apparatus 1 according to the first embodiment, the connecting tool 102A extends in the direction along the X-axis, so as to be fitted into the slits 137 formed in the plurality of first plates 111 in the collimating structure 101A and the slits 137 formed in the plurality of first plates 111 in the collimating structure 101B. As a result, the connecting tool 102A determines the positions of the plurality of first plates 111 in the collimating structure 101A and the plurality of first plates 111 in the collimating structure 101B. For example, the connecting tool 102A fitted in the slits 137 are configured to restrict the first plates 111 in the collimating structures 101A and 101B from moving in the direction along the Y-axis and the direction along the Z-axis. Consequently, it is possible to manufacture the collimator 93 more easily.

The plurality of second plates 112 are formed together with the plurality of first plates 111. Accordingly, the plurality of first plates 111 and the plurality of second plates 112 form the collimating structure 101A that is formed in the integral grid formation. Further, the plurality of first plates 111 and the plurality of second plates 112 form the collimating structure 101B. In this manner, the connecting tool 102A determines the positions of the integrally-formed collimating structure 101A and the integrally-formed collimating structure 101B. Consequently, it is possible to manufacture the collimator 93 more easily.

The connecting tool 102A is provided with the recesses 155 into which the plurality of first plates 111 in the collimating structure 101A and the plurality of first plates 111 in the collimating structure 101B are fitted. Further, the connecting tool 102B is provided with the slits 157 into which the plurality of first plates 111 in the collimating structure 101C and the plurality of first plates 111 in the collimating structure 101D are fitted. As a result, it is possible to fit the connecting tools 102 into the slits 137 from the direction along the Z-axis. Further, as a result of the plurality of first plates 111 of the collimating structure 101 being fitted in the plurality of recesses 155, the connecting tools 102 restrict the plurality of first plates 111 in the collimating structures 101 from moving in the direction along the X-axis. Consequently, it is possible to manufacture the collimator 93 more easily.

The first projecting walls 141 are disposed in the same positions as the slits 137 are, in terms of the direction along the Y-axis, so as to project from the first lateral faces 131 in the direction along the X-axis. Each of the slits 137 extends from the upper end 133 to a corresponding one of the first projecting walls 141. Further, the first projecting walls 141 are fitted in the recesses 155. Accordingly, even when the orientation direction of each of the first lateral faces 131 diagonally intersects a direction along the X-axis, because the connecting tool 102A is fitted into the slits 137 from the direction along the Z-axis, the first projecting walls 141 and the connecting tool 102A are able to form the single plate. Further, because the first projecting walls 141 are fitted in the plurality of recesses 155, the connecting tool 102A restricts the plurality of first plates 111 in the collimating structure 101A from moving in the direction along the X-axis. Consequently, it is possible to manufacture the collimator 93 more easily.

The first parts 121 in the collimating structure 101C are connected to the second parts 122 and each extend in a direction diagonally intersecting the direction along the Y-axis. The first parts 121 and the plurality of second plates 112 form the plurality of through openings 93*a*. In other words, the second parts 122 diagonally extend from the plurality of second plates 112 and the first parts 121 of the plurality of first plates 111 arranged in the grid formation. The connecting tool 102B determines the positions of the second parts 122 with respect to the second parts 122 of the first plates 111 in the collimating structure 101D. Accordingly, it is possible to diagonally connect the collimating structure 101C and the collimating structure 101D together. It is therefore possible to enhance the degree of freedom for the shape of the collimator 93.

One of the scintillators 91*a* is attached to the first plates 111 in the collimating structure 101A, and another one of the scintillators 91*a* is attached to the first plates 111 in the collimating structure 101B. As a result, by determining the positions of the first plates 111 in the collimating structures 101A and 101B, the connecting tool 102A is also able to determine the positions of the two scintillators 91*a*. Consequently, it is possible to manufacture the X-ray detector 9 more easily.

The processor used in the first embodiment may be, for example, a Central Processing Unit (CPU), a Graphics Processing Unit (GPU), an Application Specific Integrated Circuit (ASIC), a Programmable Logic Device (PLD), or a Field Programmable Gate Array (FPGA). Further, the Programmable Logic Device (PLD) may be, for example, a Simple Programmable Logic Device (SPLD) or a Complex Programmable Logic Device (CPLD).

Next, a second embodiment will be explained with reference to FIGS. 14 to 17. In the description of the plurality of embodiments presented below, some of the constituent elements having the same functions as those of already-explained constituent elements may be referred to by using the same reference characters as those for the already-explained constituent elements, and the explanations thereof may be omitted. Further, a plurality of constituent elements referred to by using mutually the same reference character do not necessarily have to share all the functions and characteristics therebetween. Those constituent elements may have mutually-different functions and characters corresponding to various embodiments.

Figure 14:
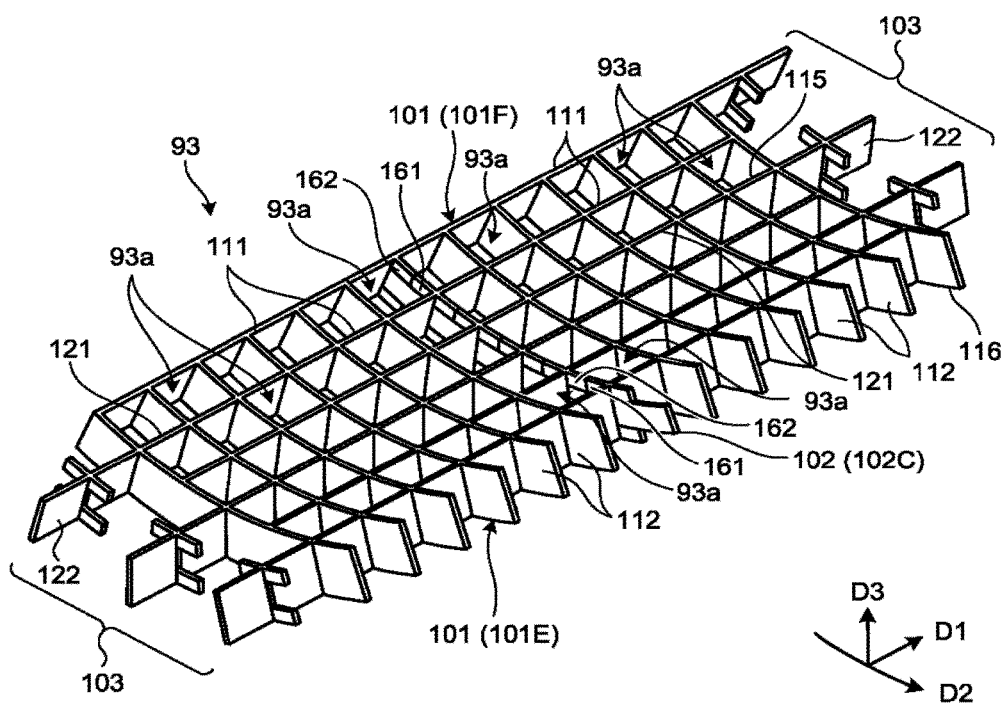
FIG. 14 is a perspective view of a part of a collimator according to a second embodiment.
Figure 15:
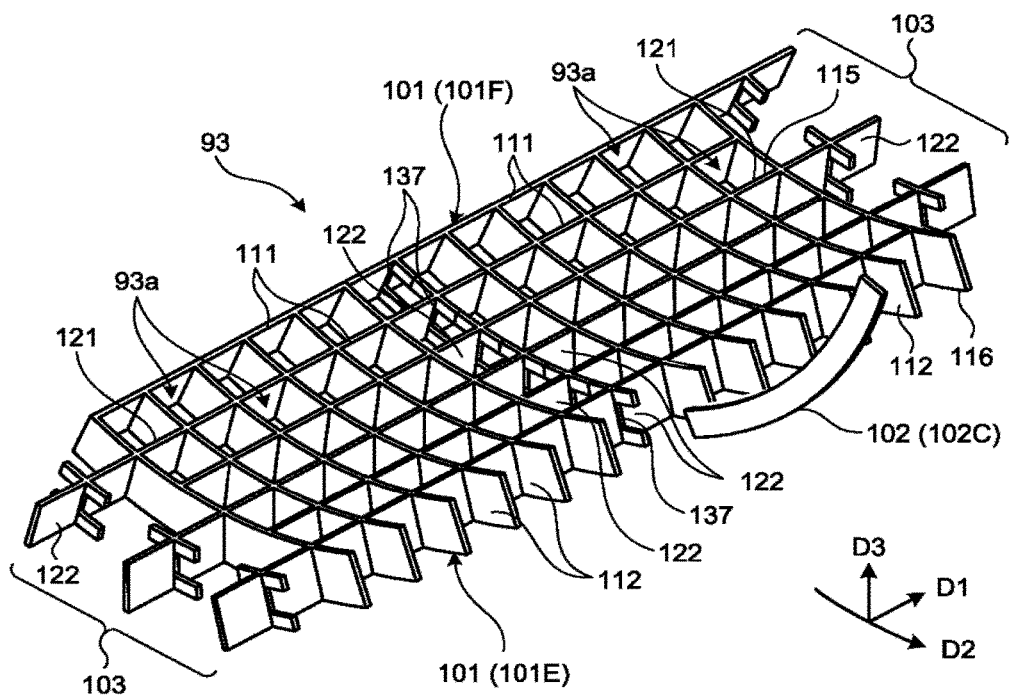
FIG. 15 is an exploded perspective view of the part of collimator according to the second embodiment.

FIG. 14 is a perspective view of a part of the collimator 93 according to the second embodiment. FIG. 15 is an exploded perspective view of a part of the collimator 93 according to the second embodiment. FIGS. 14 and 15 illustrate, from among the plurality of collimating structures 101, two collimating structures 101E and 101F as well as a connecting tool 102C.

Figure 16:
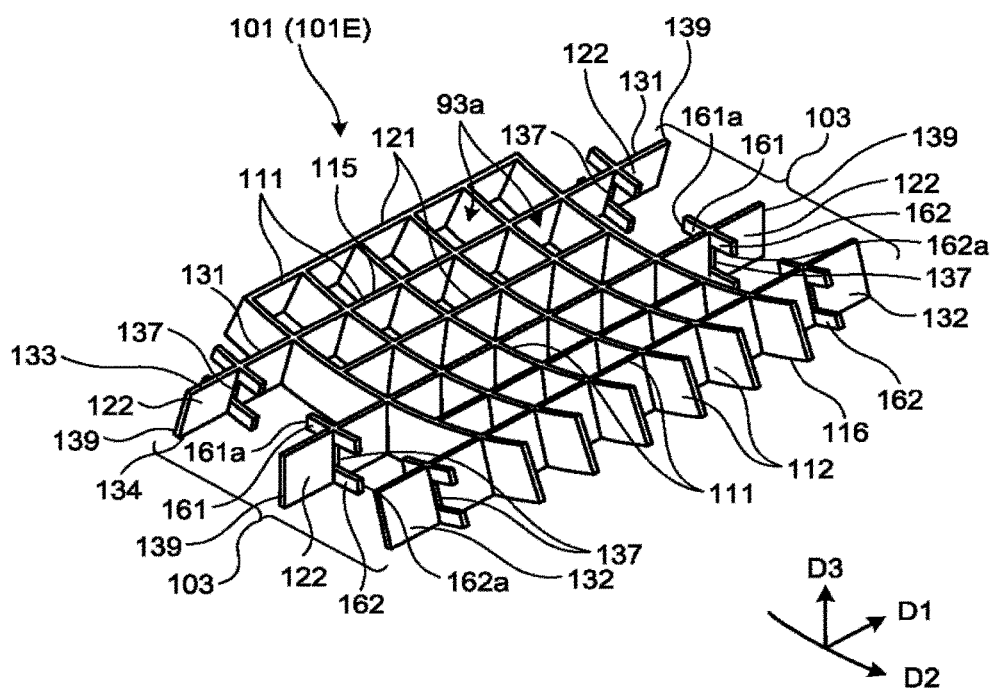
FIG. 16 is a perspective view of one of collimating structures according to the second embodiment.
Figure 17:
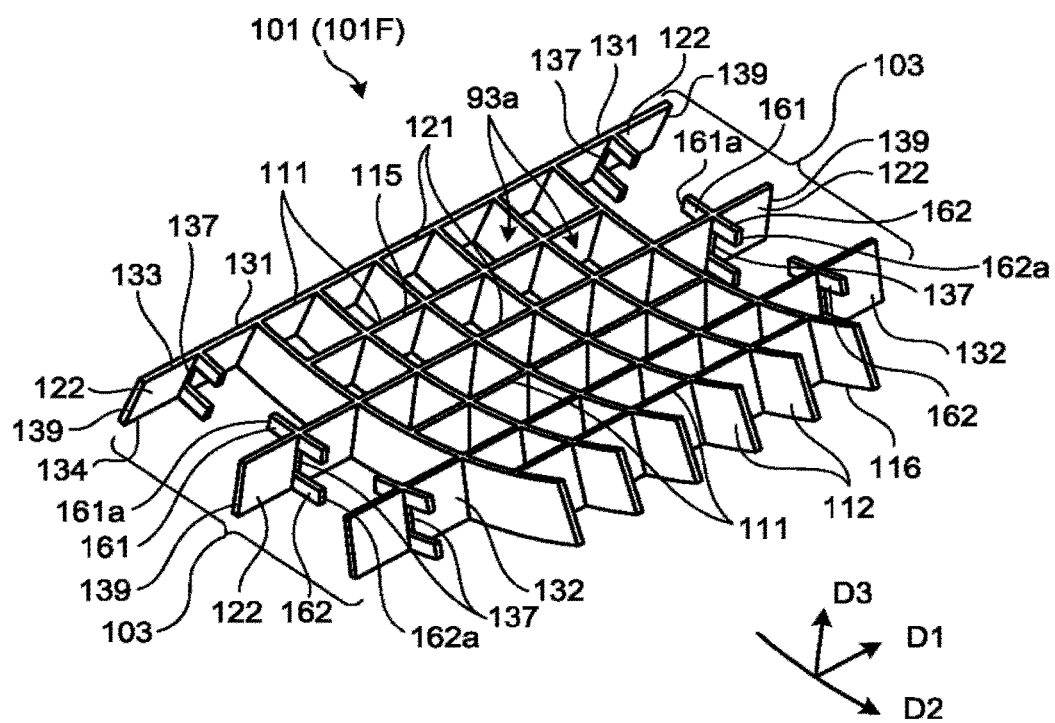
FIG. 17 is a perspective view of another one of the collimating structures according to the second embodiment.

FIG. 16 is a perspective view of the collimating structure 101E according to the second embodiment. FIG. 17 is a perspective view of the collimating structure 101F according to the second embodiment. As illustrated in FIGS. 16 and 17, the two collimating structures 101E and 101F are each in the shape of a partial cylinder sectioned in the circumferential direction. Accordingly, the top face 115 and the bottom face 116 of each of the collimating structures 101E and 110F are formed as arc-like curved planes extending substantially parallel to each other. However, the shapes of the top face 115 and the bottom face 116 of each of the collimating structures 101E and 101F are not limited to those in this example.

For reference in the following description, D1, D2, and D3 directions illustrated in the drawings will be defined as follows: The D1 direction is the direction (the axial direction) extending along the central axis, referencing the collimating structures 101E and 101F and the top face 115 and the bottom face 116 of each of the collimating structures 101E and 101F. The D2 direction is the rotating direction (the circumferential direction) centered about the central axis, referencing the collimating structures 101E and 101F and the top face 115 and the bottom face 116 of each of the collimating structures 101E and 101F. The D3 direction is the direction (the radial direction) toward the central axis, referencing the collimating structures 101E and 101F and the top face 115 and the bottom face 116 of each of the collimating structures 101E and 101F. The D1 direction and the D3 direction are orthogonal to (intersect) each other. The D2 direction is a direction on an imaginary plane orthogonal to (intersecting) the D1 direction. The D2 direction and the D3 direction illustrated in the drawings are merely examples.

The plurality of first plates 111 in each of the collimating structures 101E and 101F extend in the D1 direction. The D1 direction is an example of the first direction. The plurality of first plates 111 are arranged in a row at intervals in the D2 direction. The D2 direction is an example of the second direction.

The plurality of second plates 112 in each of the collimating structures 101E and 101F extend in the D2 direction. In other words, each of the second plates 112 extends in an arc form. The plurality of second plates 112 are arranged in a row at intervals in the D1 direction.

In each of the collimating structures 101E and 101F, the first part 121 and the second part 122 of each of the first plates 111 continuously extend in the D1 direction. The second part 122 is connected to an end of the first part 121 in terms of the D1 direction.

Each of the first lateral faces 131 in the collimating structures 101E and 101F is oriented in the D2 direction. Each of the first lateral faces 131 is oriented approximately toward the adjacently-positioned first plate 111. The first lateral face 131 of each of the collimating structure 101E and F serves as an example of the first face. Each of the second lateral faces 132 is positioned on the opposite side of a corresponding one of the first lateral faces 131. Accordingly, each of the second lateral faces 132 is oriented in the D2 direction. Each of the second lateral faces 132 is oriented approximately toward the adjacently-positioned first plate 111. The second lateral face 132 of each of the collimating structure 101E and F serves as an example of the second face.

In a planar view in the D1 direction, each of the first plates 111 having the first lateral face 131 and the second lateral face 132 as described above extends in the D3 direction. Further, in a planar view in the D2 direction, each of the second plates 112 extends in the D3 direction. However, the first plates 111 and the second plates 112 may extend in other directions.

Each of the slits 137 formed in the collimating structures 101E and 101F opens in the D2 direction. In other words, each of the slits 137 extends through a corresponding one of the second parts 122 in the D2 direction from the first lateral face 131 to the second lateral face 132.

The two ends of each of the slits 137 in terms of the D3 direction are positioned apart from the upper end 133 and the lower end 134. Accordingly, unlike the slits 137 formed in the collimating structures 101A and 101B, the slits 137 formed in the collimating structures 101E and 101F are holes. However, the slits 137 may be cut-out parts. Each of the slits 137 extends in the D3 direction.

In place of the first projecting wall 141 and the second projecting wall 142, each of the second parts 122 in the collimating structures 101E and 101F has at least one selected from between two first projecting pieces 161 and two second projecting pieces 162. The two first projecting pieces 161 in the collimating structure 101E serve as examples of the projecting part and the sixth wall. The first projecting piece 161 and the second projecting piece 162 are disposed in the same position as the slits 137 are, in terms of the D1 direction.

Each of the two first projecting pieces 161 projects from the first lateral face 131 in the D2 direction. In other words, each of the two first projecting pieces 161 projects from the first lateral face 131 toward the adjacently-positioned first plate 111. A slit 137 is positioned between the two first projecting pieces 161. Each of the first projecting pieces 161 extends in the D3 direction, similarly to the slits 137.

Each of the two second projecting pieces 162 projects from the second lateral face 132 in the D2 direction. In other words, each of the two second projecting pieces 162 projects from the second lateral face 132 toward the adjacently-positioned first plate 111. A slit 137 is positioned between the two second projecting pieces 162. Each of the second projecting pieces 162 extends in the D3 direction, similarly to the slits 137.

An end 161a of each of the first projecting pieces 161 is oriented in the D2 direction and is shaped substantially flat. An end 162a of each of the second projecting pieces 162 is oriented in the D2 direction and is shaped substantially flat. However, the ends 161a of the first projecting pieces 161 and the ends 162a of the second projecting pieces 162 may be formed to have other shapes.

On the first lateral face 131, the slit 137 extends from one of the first projecting pieces 161 to the other first projecting piece 161. On the second lateral face 132, the slit 137 extends from one of the second projecting pieces 162 to the other second projecting piece 162. In the D2 direction, the sum of the length of the first projecting piece 161 and the length of the second projecting piece 162 is substantially equal to the distance between the two adjacently-positioned first plates 111.

As illustrated in FIG. 15, each of the second parts 122 in the collimating structure 101F is positioned between corresponding two of the second parts 122 in collimating structure 101E that are positioned adjacent thereto in the D2 direction. The slits 137 formed in the second parts 122 of the collimating structure 101E and the slits 137 formed in the second parts 122 of the collimating structure 101F are arranged in a row in the D2 direction.

The first projecting pieces 161 and the second projecting pieces 162 in the collimating structure 101E and the first projecting pieces 161 and the second projecting pieces 162 in the collimating structure 101F are arranged in a row in the D2 direction. The end 161a of each of the first projecting pieces 161 in the collimating structure 101E is in contact with the end 162a of a corresponding one of the second projecting pieces 162 in the collimating structure 101F. In other words, each of the first projecting pieces 161 in the collimating structure 101E is in contact with a corresponding one of the second parts 122 in the collimating structure 101F.

The end 162a of each of the second projecting pieces 162 in the collimating structure 101E is in contact with the end 161a of a corresponding one of the first projecting pieces 161 in the collimating structure 101F. In other words, each of the second projecting pieces 162 in the collimating structure 101E is in contact with a corresponding one of the second parts 122 in the collimating structure 101F.

The connecting tool 102C extends in the D2 direction. In other words, the connecting tool 102C extends parallel to the plurality of second plates 112 in the collimating structure 101E and also extends parallel to the plurality of second plates 112 in the collimating structure 101F. Further, in a planar view in the D2 direction, the connecting tool 102C extends in the D3 direction.

The connecting tool 102C is fitted into the slits 137 formed in the plurality of first plates 111 in the collimating structure 101E and the slits 137 formed in the plurality of first plates 111 in the collimating structure 101F. The connecting tool 102 is inserted in the D2 direction into the plurality of slits 137. When the connecting tool 102C has been fitted in the slits 137, the connecting tool 102C restricts the first plates 111 in the collimating structures 101E and 101F from moving in the D1 direction and the D3 direction.

As explained above, each of the first projecting pieces 161 and the second projecting pieces 162 in the collimating structure 101E is in contact with a corresponding one of the first projecting pieces 161 and the second projecting pieces 162 in the collimating structure 101F. Accordingly, the first plates 111 in the collimating structures 101E and 101F are restricted from moving in the D2 direction.

In the manner described above, the connecting tool 102C is fitted in the slits 137 formed in the collimating structures 101E and 101F. As a result, the connecting tool 102C is attached to the collimating structures 101E and 101F so as to connect together the collimating structure 101E and the collimating structure 101F.

For example, the connecting tool 102C determines the positions of the collimating structure 101E and the collimating structure 101F. In that state, the collimating structures 101E and 101F and the connecting tool 102C are fixed to each other, by using an adhesive agent, for example. However, the collimating structures 101E and 101F and the connecting tool 102C may be fixed to each other by using other means. Alternatively, the collimating structures 101E and 101F and the connecting tool 102C do not necessarily have to be fixed to each other.

As illustrated in FIG. 14, when the connecting tool 102C has been attached to the collimating structures 101E and 101F, the connecting tool 102C, the first projecting pieces 161, and the second projecting pieces 162 form a single plate. The connecting tool 102C fitted in the slits 137, the first projecting pieces 161, and the second projecting pieces 162 form the plurality of through openings 93a, together with the first plates 111 and the second plates 112 in the collimating structures 101E and 101F.

In the X-ray CT apparatus 1 according to the second embodiment, the connecting tool 102C is inserted into the slits 137 along the extending direction of the second plates 112. As a result, it is possible to easily fit the connecting tool 102C into the plurality of slits 137.

The first projecting pieces 161, the second projecting pieces 162, and the connecting tool 102C fitted in the slits 137 form the plurality of through openings 93a, together with the first plates 111 and the second plates 112 in the collimating structures 101E and 101F. In other words, the plurality of through openings 93a are also formed in the part where the second parts 122 in the collimating structure 101E are connected to the second parts 122 in the collimating structure 101F. Consequently, it is possible to prevent the level of performance of the collimator 93 from being degraded.

In the second embodiment, the top face 115 and the bottom face 116 in each of the collimating structures 101E and 101F are formed as the arc-like curved planes extending substantially parallel to each other. However, the top face 115 and the bottom face 116 of each of the collimating structures 101E and 101F may be formed as flat planes extending substantially parallel to each other.

In the above situation, the first projecting pieces 161 and the second projecting pieces 162 project in the extending direction of the second plates 112 (the direction along the X-axis). Further, the connecting tool 102 extends in the extending direction of the second plates 112 (the direction along the X-axis) and is inserted in the direction along the X-axis into the slits 137.

Figure 18:
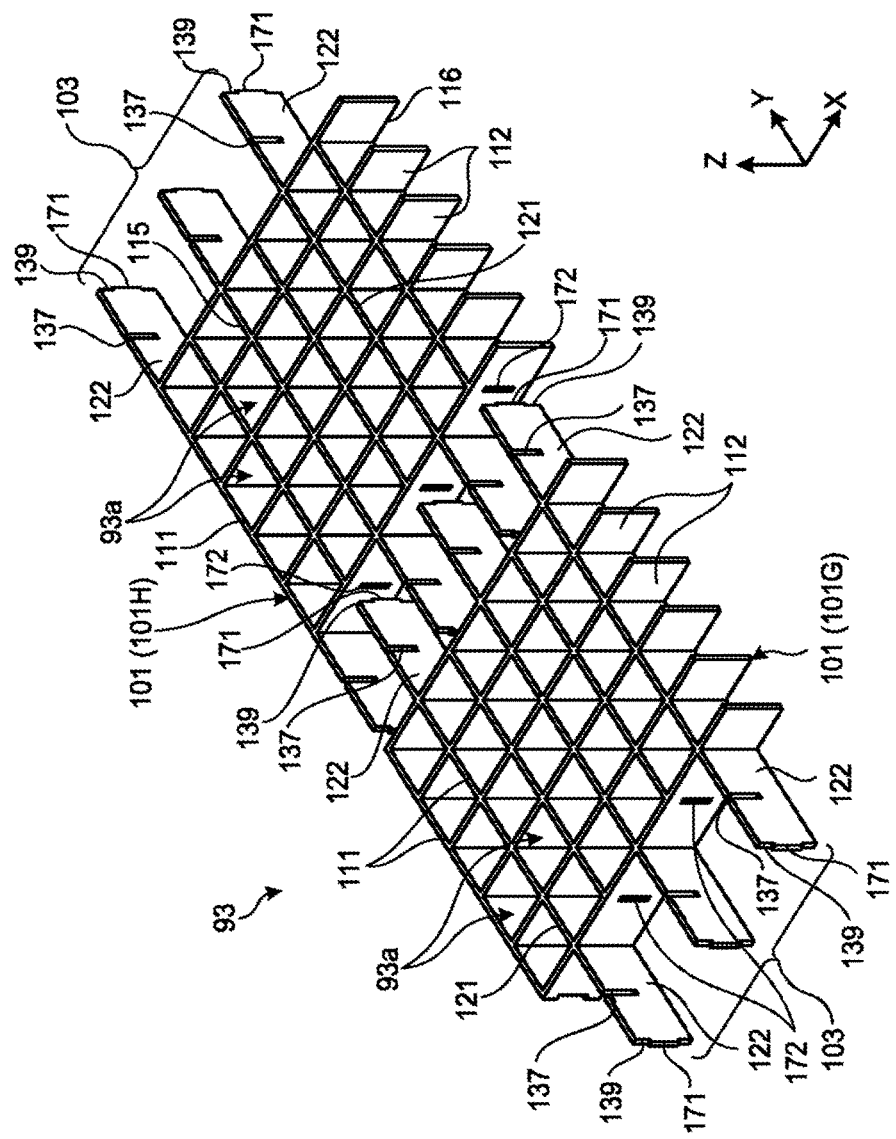
FIG. 18 is an exploded perspective view of a part of a collimator according to a third embodiment.

Next, a third embodiment will be explained, with reference to FIG. 18. FIG. 18 is an exploded perspective view of a part of the collimator 93 according to the third embodiment. As illustrated in FIG. 18, the second part 122 of one or more of the first plates 111 in the third embodiment has a protrusion 171. The protrusion 171 is an example of the first holding part. At least one of the first plates 111 has the protrusion 171.

The protrusion 171 is provided on an end face 139 of at least one of the first plates 111. The protrusion 171 protrudes from the end face 139 in a direction along the Y-axis. In other words, the protrusion 171 protrudes in the extending direction of the second part 122 of the first plate 111.

The length of the protrusion 171 in the direction along the Y-axis is shorter than the length (the thickness) of the second plate 112 in the direction along the Y-axis. However, the length of the protrusion 171 in the direction along the Y-axis may be equal to or may be longer than the thickness of the second plates 112.

In a single collimating structure 101, a plurality of dents 172 are formed in the second plate 112 positioned at an end among the plurality of arranged second plates 112. In other words, the plurality of dents 172 are formed in the second plate 112 positioned adjacent to the connecting tool 102. The dents 172 serve as an example of the second holding part.

The protrusions 171 are fitted in the dents 172. For example, the protrusions 171 formed on the first plates 111 of one of the collimating structures 101 (101G) are fitted in the dents 172 formed in the second plates 112 of the other collimating structure 101 (101H).

The protrusions 171 are in contact with the inner surfaces of the dents 172 formed in the other collimating structure 101 (101H) that is prone to move in the direction intersecting the Y-axis relative to the first plates 111 in the one of the collimating structure 101 (101G). As a result, the protrusions 171 and the dents 172 restrict the two collimating structures 101 from moving relatively in the direction intersecting the Y-axis.

In the X-ray CT apparatus 1 according to the third embodiment, at least one of the first plates 111 has the end face 139 of the second part 122 in terms of the direction along the Y-axis and the protrusion 171 provided on the end face 139. The second plate 112 positioned adjacent to the connecting tool 102 has the dents 172. The protrusions 171 are in contact with the dents 172 formed in the second plate 112 prone to move in the direction intersecting the direction along the Y-axis relative to the first plates ill. In other words, the protrusions 171 and the dents 172 determine the positions of the first plates 111 and the second plates 112 in the one of the collimating structure 101 (101G) and the first plates 111 and the second plates 112 in the other collimating structure 101 (101H). The connecting tool 102 is fitted in the slits 137 formed in the two collimating structures 101 of which the positions are determined by the protrusions 171 and the dents 172. Consequently, it is possible to easily manufacture the collimator 93.

In the plurality of embodiments described above, the plurality of first plates 111 and the plurality of second plates 112 are integrally formed. However, the plurality of first plates 111 may detachably attached to the plurality of second plates 112. For example, the plurality of second plates 112 may be configured to have the same shape as that of the connecting tool 102, so as to be fitted into the slits 137 formed in the first plates 111.

According to at least one aspect of the embodiments described above, the collimator is structured by connecting together the plurality of modules each having the grid formation. With this arrangement, it is possible to easily manufacture the collimator.

While a number of embodiments of the present disclosure have been described, these embodiments are presented by way of examples only, and are not intended to limit the scope of the invention. These novel embodiments may be carried out in a variety of other forms. Also, various omissions, substitutions, and changes may be made without departing from the gist of the invention. These embodiments and modifications thereof are covered in the scope and the gist of the invention and are also covered by the invention defined in the claims and their equivalents.

The invention claimed is:

1. A collimator comprising:
   a plurality of modules each of which has a grid formation and in each of which a plurality of walls are arranged in a row in a first direction and a second direction intersecting the first direction;
   a connecting part having at least one plate-like member that is provided at an end of each of the plurality of modules and that projects in the first direction; and
   a connector combined, in a grid formation, with the connecting parts of adjacently-positioned modules in the plurality of modules, and configured to connect the adjacently-positioned modules in the first direction, wherein
   each of the plurality of modules includes the plurality of walls that include a plurality of first walls arranged in a row at intervals in the second direction and a plurality of second walls arranged in a row at intervals in the first direction,
   the connecting part includes a first face oriented in the second direction, a second face positioned on the opposite side of the first face and oriented in the second direction, two projecting parts that project from the first face in the second direction, and a first opening formed between the two projecting parts and extending through the connecting part in the second direction from the first face to the second face,
   the connector extends in the second direction, and is configured to be inserted through and fitted in the first openings of the connecting parts of the adjacently-positioned modules in a state that the connecting parts of the adjacently-positioned modules are arranged in a row at intervals in the second direction and that the two projecting parts of one of the adjacently-positioned modules are in contact with the connecting part of the other of the adjacently-positioned modules, and
   when the connector has been fitted in the first openings of the connecting parts of the adjacently-positioned modules, the connector and the two projecting parts form a single wall and accordingly form a plurality of through openings together with the first and the second walls.

2. The collimator according to claim 1, wherein
   the plurality of second walls are formed together with the plurality of first walls.

3. The collimator according to claim 1, wherein
the connecting part has an end face in the first direction and,
a first holding part provided on the end face,
a second wall positioned adjacent to the connecting part has a second holding part, and
the first holding part of the one of the adjacently-positioned modules is configured to be in contact with the second holding part provided on the second wall of the other of the adjacently-positioned modules that is prone to move in a direction intersecting the first direction relative to the first wall.

4. The collimator according to claim 1, wherein each of the plurality of first walls is connected to the first connecting part, extends in a direction diagonally intersecting the first direction, and forms the plurality of through openings together with the plurality of second walls.

5. A radiation detector comprising:
the collimator according to claim 1;
a plurality of scintillators each of which faces a different one of the plurality of through openings formed by the plurality of walls; and
a plurality of detecting parts each of which is configured to detect light and faces a different one of the plurality of scintillators.

6. The radiation detector according to claim 5, wherein
one of the plurality of scintillators is attached to one of the plurality of modules, while another one of the plurality of scintillators is attached to another one of the plurality of modules, and
the one of the modules and said another one of the modules are connected together by the connecting part.

7. A radiation examination apparatus comprising:
the radiation detector according to claim 5; and
a radiation source configured to emit radiation toward the radiation detector.

* * * * *